US010765727B2

(12) United States Patent
Lyday et al.

(10) Patent No.: US 10,765,727 B2
(45) Date of Patent: *Sep. 8, 2020

(54) COMPOSITIONS AND METHODS FOR PRODUCING DENDRITIC CELLS

(71) Applicant: PrimeVax Immuno-Oncology, Inc., Orange, CA (US)

(72) Inventors: Bruce W. Lyday, Orange, CA (US); Tony Chen, Jersey City, NJ (US)

(73) Assignee: Primevax Immuno-Oncology, Inc., Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/275,073

(22) Filed: Sep. 23, 2016

(65) Prior Publication Data
US 2017/0087233 A1 Mar. 30, 2017

Related U.S. Application Data

(60) Provisional application No. 62/284,434, filed on Sep. 26, 2015.

(51) Int. Cl.
A61K 39/00 (2006.01)
C12N 5/0784 (2010.01)
A61K 39/12 (2006.01)
A61K 35/768 (2015.01)
C12N 7/00 (2006.01)
A61K 39/39 (2006.01)

(52) U.S. Cl.
CPC ........ *A61K 39/0011* (2013.01); *A61K 35/768* (2013.01); *A61K 39/39* (2013.01); *C12N 5/0639* (2013.01); *C12N 7/00* (2013.01); *A61K 2039/5154* (2013.01); *A61K 2039/525* (2013.01); *A61K 2039/5254* (2013.01); *A61K 2039/55511* (2013.01); *A61K 2039/55522* (2013.01); *A61K 2039/55533* (2013.01); *A61K 2039/55588* (2013.01); *A61K 2039/585* (2013.01); *C12N 2501/05* (2013.01); *C12N 2501/052* (2013.01); *C12N 2501/24* (2013.01); *C12N 2501/999* (2013.01); *C12N 2770/24132* (2013.01); *C12N 2770/24171* (2013.01); *Y02A 50/386* (2018.01)

(58) Field of Classification Search
None
See application file for complete search history.

(56) References Cited

U.S. PATENT DOCUMENTS

| 6,048,686 | A | 4/2000 | Lyday |
| 6,511,667 | B1 | 1/2003 | Eckels et al. |
| 6,524,587 | B1 | 2/2003 | Lyday |
| 7,217,418 | B2 | 5/2007 | Eckels et al. |
| 8,415,152 | B2 | 4/2013 | Muhlradt et al. |
| 8,889,118 | B2 | 11/2014 | Okano et al. |
| 9,849,167 | B2 | 12/2017 | Lyday |
| 2002/0146396 | A1 | 10/2002 | Albert et al. |
| 2007/0065467 | A1 | 3/2007 | Krieg et al. |
| 2007/0082400 | A1* | 4/2007 | Healey ............... C12N 5/0639 435/459 |
| 2007/0087015 | A1 | 4/2007 | Eckels et al. |
| 2013/0089567 | A1 | 4/2013 | Whitehead et al. |
| 2013/0183343 | A1* | 7/2013 | Czerniecki ............ A61K 39/00 424/234.1 |
| 2015/0166532 | A1 | 6/2015 | Gray et al. |
| 2016/0058852 | A1 | 3/2016 | Ter Meulen et al. |
| 2018/0050098 | A1 | 2/2018 | Lyday |
| 2019/0247479 | A1 | 8/2019 | Lyday |
| 2019/0298764 | A1 | 10/2019 | Lyday |

FOREIGN PATENT DOCUMENTS

| WO | WO-0057705 A1 | 10/2000 |
| WO | WO-0156599 A2 | 8/2001 |
| WO | WO-2008022196 A2 | 2/2008 |
| WO | WO-2012160199 A1 | 11/2012 |
| WO | WO-2013188315 A1 | 12/2013 |
| WO | WO-2016179475 A1 | 11/2016 |
| WO | WO-2017004567 A1 | 1/2017 |
| WO | WO-2017053873 A1 | 3/2017 |
| WO | WO-2018093907 A1 | 5/2018 |
| WO | WO-2018129202 A1 | 7/2018 |
| WO | WO-2018232166 A1 | 12/2018 |

OTHER PUBLICATIONS

Turnis et al., 2010, Immunother. vol. 2: 847-862.*
Xu et al., 2006, Surgery, vol. 140: 170-178.*
Napolitani et al., 2005, Nat. Innnnunol. vol. 6: 769-776.*
Gervais et al. In vitro antitumor lymphocyte generation using dendritic cells and innate immunity mechanisms as tumor cell treatments. Anticancer Res 27(4B):2385-2392 (2007).
Ma et al. The TLR7 agonists imiquimod and gardiquimod improve DC-based immunotherapy for melanoma in mice. Cell Mol Immunol 7(5):381-388 (2010).
PCT/US2016/040787 International Search Report and Written Opinion dated Sep. 22, 2016.
PCT/US2016/053554 Invitation to Pay Additional Fees dated Nov. 28, 2016.

(Continued)

*Primary Examiner* — Amy E Juedes
(74) *Attorney, Agent, or Firm* — Wilson Sonsini Goodrich & Rosati

(57) ABSTRACT

Described herein are compositions and methods for treating a disease, particularly a cancer, with primed dendritic cells recognizing a tumor antigen. The methods may comprise storing, shipping and/or culturing dendritic cells, where the dendritic cells are stored on a hard surface. Lysis protocols are described where the lysis does not result in complete lysis of cells in order to provide cell surface molecules maintained in a cell surface-embedded state. Non-lethal Dengue virus strains are also provided for therapeutic purposes.

Figure 1:
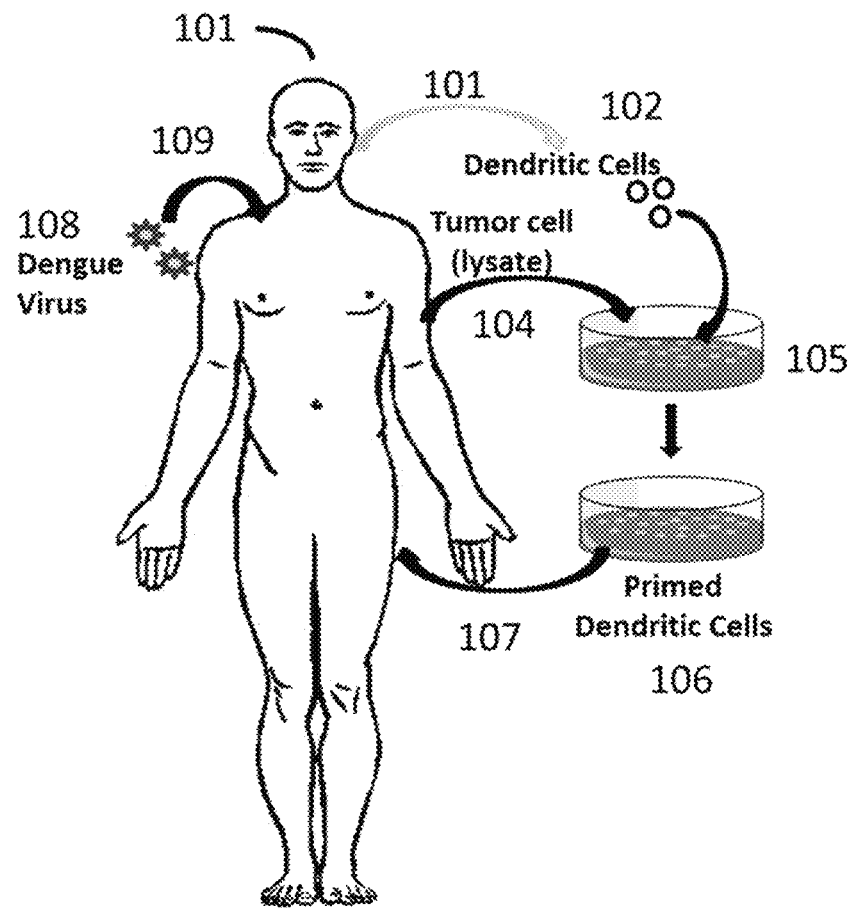
Figure 2:
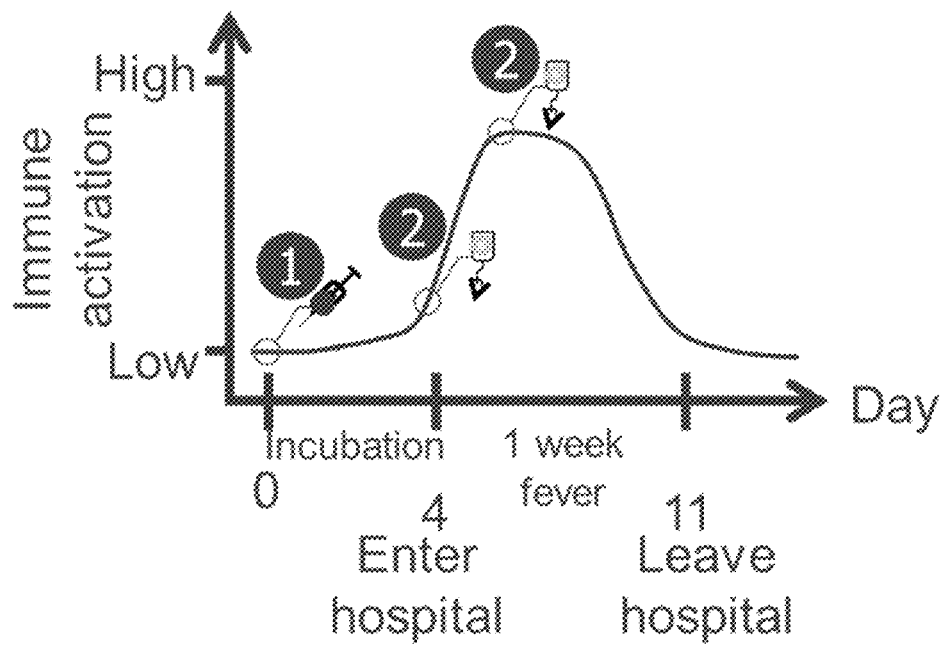
Figure 2:
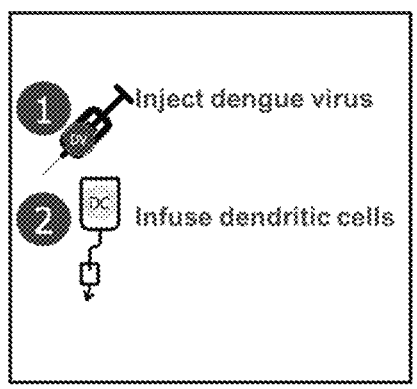

11 Claims, 6 Drawing Sheets
Specification includes a Sequence Listing.

(56) References Cited

OTHER PUBLICATIONS

Angsubhakorn et al. Neurovirulence detection of dengue virus using rhesus and cynomolgus monkeys. J Virol Methods 18(1):13-24 (1987).

Anguille et al. Clinical use of dendritic cells for cancer therapy. Lancet Oncol 15:e257-267 (2014).

Carreno et al. IL-12p70-producing patient DC vaccine elicits Tc1-polarized immunity. J Clin Invest 123(8):3383-3394 (2013).

Chalaem et al. Characterization of a Chikungunya virus strain isolated from banked patients' sera. Virol J 13(1):150 (2016).

Chiang et al. Optimizing parameters for clinical-scale production of high IL-12 secreting dendritic cells pulsed with oxidized whole tumor cell lysate. J Transl Med 14;9:198 (2011).

Co-pending U.S. Appl. No. 15/200,751, filed Jul. 1, 2016.

Dillman et al. High-dose IL2 in metastatic melanoma: better survival in patients immunized with antigens from autologous tumor cell lines. Cancer Biother Radiopharm 29(2):53-57 (2014).

Eckels et al. Isolation of a Temperature—Sensitive Dengue—2 Virus Under Conditions Suitable for Vaccine Development. Infect Immun 14(5):1221-1227 (1976).

Gabrilovitch et al. Dendritic cells in antitumor immune responses. II. Dendritic cells grown from bone marrow precursors, but not mature DC from tumor-bearing mice, are effective antigen carriers in the therapy of established tumors. Cell Immunol 70(1):111-119 (1996).

Hahn et al. Nucleotide sequence of dengue 2 RNA and comparison of the encoded proteins with those of other flaviviruses. Virology 162:167-180 (1988).

Halstead. Etiologies of the Experimental Dengues of Siler and Simmons. Am J Trop Med Hys 23:974-982 (1974) (http://www.ajtmh.org/content/23/5/974.long).

Harris et al. Rapid subtyping of dengue viruses by restriction site-specific (RSS)-PCR. Virology 253:86-95 (1999).

Islas-Rodríguez et al. Effect of in vitro infection with dengue virus (DEN-2) on various cellular immune response functions in the mouse. Archivos de Investiga cion Medica 21(2):87-93 (1990) (English Abstract).

Kurane et al. Activation of T lymphocytes in dengue virus infections. High levels of soluble interleukin 2 receptor, soluble CD4, soluble CD8, interleukin 2, and interferon-gamma in sera of children with dengue. J Clin Invest 88:1473-1480 (1991).

Kuss et a. Clinical significance of decreased zeta chain expression in peripheral blood lymphocytes of patients with head and neck cancer. Clin Cancer Res 5:329-334(1999).

Linette et al. Cardiovascular toxicity and titin cross-reactivity of affinity-enhanced T cells in myeloma and melanoma. Blood 122(6):863-871 (2013).

Lutz et al. An advanced culture method for generating large quantities of highly pure dendritic cells from mouse bone marrow. J Immunol Methods 223:77-92 (1999).

Lyday et al. Overcoming tumor immune evasion with an unique arbovirus. J Transl Med 13:3 (2015) (12 pgs).

MACS® GMP Cell Differentiation Bag. Miltenyi Biotec Product Insert. Issued: Aug. 2012 (2 pgs).

Mettler et al. Virus Inoculation in Mice Bearing Ehrlich Ascitic Tumors: Antigen Production and Tumor Regression. Infect Immun 37(1):23-27 (1982).

Mizoguchi et al. Alterations in signal transduction molecules in T lymphocytes from tumor-bearing mice. Science 258:1795-1798 (1992).

Nunes et al. Emergence and potential for spread of Chikungunya virus in Brazil. BMC Medicine 13:102 (2015).

Pfeiffer. Dissertation—Generation of effective designer dendritic cells for therapeutic cancer vaccination using RNA electroporation. The Faculty of Science, University of Erlangen-Nuremberg (146 pgs) (2013) (w/English translation).

Rouas et al. Dendritic cells generated in clinical grade bags strongly differ in immune functionality when compared with classical DCs generated in plates. J Immunother 33(4):352-363 (2010).

Sheikh et al. Sipuleucel-T immune parameters correlate with survival: an analysis of the randomized phase 3 clinical trials in men with castration-resistant prostate cancer. Cancer Immunol Immunother 62(1):137-147 (2013).

Sinkovics et al. New Developments in the Virus Therapy of Cancer: A Historical Review. Intervirology 36:193-214 (1993).

Straussman et al. Tumour micro-environment elicits innate resistance to RAF inhibitors through HGF secretion. Nature 487:500-504 (2012).

Taweechaisupapong et al. Langerhans cell density and serological changes following intradermal immunisation of mice with dengue 2 virus. J Med Microbiol 45:138-145 (1996).

Wolchok et al. Nivolumab plus ipilimumab in advanced melanoma. N Eng J Med. 369:122-133(2013).

Andersen et al. Spontaneous immunity against Bcl-xL in cancer patients. J Immunol 175(4):2709-2714 (2005).

Armstrong et al. Efficiency of dengue serotype 2 virus strains to infect and disseminate in Aedes aegypti. Am J Trop Med Hyg 68:539-544 (2003).

Balmaseda et al. Serotype-Specific Differences in Clinical Manifestations of Dengue. Am J Trop Med Hyg 74(3):489-456 (2006).

Bente et al. Dengue Fever in Humanized NOD/SCID Mice. J Virol 79(21):13797-13799 (2005).

Bozza et al. Multiplex cytokine profile from dengue patients: MIP-1b and IFN-gamma as predictive factors for severity. BMC Infect Dis 8:86-93 (2008).

Cabrera et al. Analysis of HLA expression in human tumor tissues. Cancer Immunol Immunother 52:1-9 (2003).

Chakraborty et al. Emergence of regulatory CD4+ T cell responses to repetitive stimulation with antigen-presenting cells in vitro: implications in designing APC-based tumor vaccines. J Immunol 162:5576-5583 (1999).

Chang et al. Production of IL-1 by human monocytes exposed to dengue virus. J Infect Dis 170:811-817 (1994).

Chen et al. Activation of terminally differentiated human monocytes/macrophages by dengue virus: productive infection, hierarchical production of innate cytokines and chemokines, and the synergistic effect of lipopolysaccharide. J Virology 76:9877-9887 (2002).

Crooks et al. The use of the Karnofsky Performance Scale in determining outcomes and risk in geriatric outpatients. J Gerontol 46:M139-M144 (1991).

De Haan et al. Measuring quality of life in stroke. Stroke 24:320-327 (1993).

Den Boer et al. Longevity of antigen presentation and activation status of APC are decisive factors in the balance between CTL Immunity Vs. Tolerance. J Immunol 167:2252-2258 (2001).

Dengue: Guidelines for Diagnosis, Treatment, Prevention and Control. World Health Organization (160 pgs) (2009).

Dequen et al. Systematic review and network meta-analysis of overall survival comparing 3 mg/kg Ipilimumab with alternative therapies in the management of pre-treated patients with unresectable Stage III or IV melanoma. Oncologist 17(11):1376-1385 (2012).

Diamond et al. Infection of human cells by dengue virus is modulated by different cell types and viral strains. J Virology 74(17):7814-7823 (2000).

Doyle et al. 9.1.1 Principles Governing the Use of Cancer Chemotherapy in Palliative Care. Oxford Textbook of Palliative Medicine, Oxford University Press. (p. 255) (1993).

Draghiciou et al. Therapeutic immunization and local low-dose tumor irradiation, a reinforcing combination. Int J Cancer 177(3):311-327 (2012).

Dudek et al. Inducers of Immunogenic Cancer Cell Death. Cytokine Growth Factor Rev 24(4):319-333 (2013).

Ellem et al. The labyrinthine ways of cancer immunotherapy-T cell, tumor cell encounter: 'How do I lose thee? Let me count the ways'. Ad Cancer Res 75:203-249 (1998).

Endy. Human immune responses to dengue virus infection: lessons learned from prospective cohort studies. Front Immunol 5:183 (2014).

Fracol et al. Response to HER-2 pulsed DC1 vaccines is predicted by both HER-2 and estrogen receptor expression in DCIS. Ann Surg Oncol 20(10):3233-3239 (2013).

(56) References Cited

OTHER PUBLICATIONS

Franciszkiewicz et al. CD103 or LFA-1 engagement at the immune synapse between cytotoxic T cells and tumor cells promotes maturation and regulates T-cell effector functions. Cancer Res 73(2):617-628 (2013).
Ganss et al. Combination of T-cell therapy and trigger of inflammation induces remodeling of the vasculature and tumor eradication. Cancer Research 62:1462-1470 (2002).
George et al. Chapter 5: Clinical spectrum of dengue infection. Dengue and Dengue Hemorrhagic Fever (Gubler and Kuno, CAB International) (25 pgs) (1997).
Gottardis et al. Estradiol-stimulated growth of MCF-7 tumors implanted in athymic mice: a model to study the tumoristatic action of tamoxifen. J Steroid Biochem 30: 311-314 (1988).
Gupta et al. Acute disseminated encephalomyelitits associated with dengue infection, a case report with literature review. J Neurol Sci 335(1-2):216-218 (2013).
Habaragamuwa et al. N-acetylcystein in dengue-associated severe hepatitis. Indian J Crit Care Med 18(3):181-184 (2014).
Heylmann et al. Radiation sensitivity of human and murine peripheral blood lymphocytes, stem, and progenitor cells. Biochim Biophys Acta 1846(1):121-129 (2014).
Hober et al. High levels of sTNFR p75 and TNF alpha in dengue-infected patients. Microbiol Immunol 40:569-573 (1996).
Hollen et al. Measurement of quality of life in patients with lung cancer in multicenter trials of new therapies. Cancer 73:2087-2098 (1994).
Hung. Fluid Management for dengue in children. Paediatrics and Child Health 32(S-1):39-42 (2012).
Janikashvili et al. Personalized dendritic cell-based tumor immunotherapy. Immunotherapy 2(1):57-68 (2010).
Kelley et al. Dengue Hemorrhagic Fever-Associated Immunomediators Induced via maturation of Dengue Virus Nonstructural 4B Protein in Monocytes Modulate Endothelial Cell Adhesion Molecules and Human Microvascular Endothelial Cells Permeability. Virology 422(2):326-337 (2012).
Khan et al. The Evolving Role of Radiation Therapy in the Management of Malignant Melanoma. Int J Radiat Oncol Biol Phys 80(3):645-654 (2011).
Kuo et al. Liver biochemical tests and dengue fever. Am J Trop Med Hyg 47:265-270 (1992).
Kurane et al. Dengue virus infection of human skin fibroblasts in vitro production of IFN-Beta, IL-6, and GM-CSF. Arch Virol 124:21-30 (1992).
Kurlander et al. A functional comparison of mature human dendritic cells prepared in fluorinated ethylene-propylene bags or polystyrene flasks. Transfusion 46(9):1494-1504 (2006).
Lee et al. Acute myocarditis in dengue hemorrhagic fever: a case report and review of cardiac complications in dengue-affected patients. Int J Infect Dis 14:e919-e922 (2010).
Lee et al. Clinical characteristics, risk factors, and outcomes in adults experiencing DHF complicated with acute renal failure. Am J Trop Med Hyg 80(4): 651-655 (2009).
Leitmeyer et al. Dengue Virus structural changes that correlate with pathogenesis. J Virol 73:4738-4747 (1999).
Lesterhaus et al. Dendritic Cell vaccines in melanoma: from promise to proof? Crit Rev Oncol Hematol 66(2):118-134 (2008).
Lizarraga et al. Dengue-associated kidney disease. J Nephropathol 3(2):57-62 (2014).
Lum et al. Dengue-associated adult respiratory distress syndrome. Ann Trop Paediatr 15(4):335-339 (1995).
Malavige et al. T cell responses in dengue viral infections. J Clin Virol 58(4):605-611 (2013).
Malik et al. Dengue encephalopathy-still and enigma? J Infect Dev Ctries 8(8):1076-1078 (2014).
Matthew et al. Dominant recognition by human CD8+ CTL of dengue virus non-structural proteins NS3 and NS1.2a. J Clin Invest 98:1684-1691 (1996).
McKee et al. Lack of attenuation of a candidate Dengue-1 vaccine (45AZ5), in human volunteers. Am J Trop Med Hyg Mar 36:435-442 (1987).
Mittendorf et al. Final report of the phase I/II clinical trial of the E75 (nelipepimut-S) vaccine with booster inoculations to prevent disease recurrence in high-risk breast cancer patients. Ann Oncol 25(9):1735-1742 (2014).
Morse et al. Migration of human DC after injection in Patients with Metastatic Malignancies. Cancer Res 59:56-58 (1999).
Nakai et al. Immunoregulatory T cells in the peripheral blood of melanoma patients treated with melanoma antigen-pulsed dendritic cell vaccination. J Dermatol Sci 54:31-37 (2009).
Nava et al. An optimized method for manufacturing a clinical-scale Dendritic Cell-based vaccine for the treatment of Glioblastoma. PLoS One 7(12):e52301 (2012).
Nielsen. The Relationship of intersecting immunological components in Dengue pathogenesis. Virol J 6:1-7 (2009).
Nocera et al. Restoring Lost Anti-HER-2 Th1 Immunity in Breast Cancer: A Crucial Role for Th1 Cytokines in Therapy and Prevention. Front Pharmacol 7:356 (2016).
Oken et al. Toxicity and Response Criteria of the Eastern Cooperative Oncology Group. Am J Clin Oncol 5:649-655 (1982).
Oleinika et al. Suppression, subversion, and escape: the role of regulatory T cells in cancer progression. Clin Exp Immunol 171:36-45 (2012).
Olszanski. Current and Future Roles of Targeted Therapy and Immunotherapy in Advanced Melanoma. J Manag Care Pharm 20(4):346-354 (2014).
Osborne et al. Effects of estrogens and antiestrogens on growth of human breast cancer cells in athymic nude mice. Cancer Res 45:584-590 (1985).
O'Toole et al. Evaluating cancer patients for rehabilitation potential. West J Med 155:384-387 (1991).
Park et al. Radiation-induced vascular damage in tumors: implications of vascular damage in ablative hypofractionated radiotherapy (SBRT and SRS). Radiat Res 177(3):311-327 (2012).
Pasca et al. Role of Interleukin-12 in patients with dengue hemorrhagic fever. FEMS Immunol Med Microbiol 28:151-155 (2000).
PCT/US2016/053554 International Search Report and Written Opinion dated Feb. 3, 2017.
Prestwich et al. The case of oncolytic viruses versus the immune system: waiting on the judgment of Solomon. Hum Gene Ther 20(10):1119-1132 (2009).
Rajat et al. Unusual manifestations in dengue outbreak 2009, Delhi, India. J Communicable Dis 42(4):255-261 (2010).
Schag et al. Karnofsky performance status revisited: Reliability, validity,and guidelines. J Clin Oncol 2:187-193 (1984).
Sharma et al. Guillain-Barre syndrome occurring during dengue fever. J Indian Med Assoc 109(9):675 and 682 (2011).
Singhi et al. Dengue and Dengue Hemorrhagic Fever: management issues in an intensive care unit. J Pediatr (Rio J) 83(Supp 2):S22-S35 (2007).
Sorlie et al. Gene expression patterns of breast carcinomas distinguish tumor subclasses with clinical implications. PNAS USA 98:10869-10874 (2001).
Stanton et al. Clinical significance of tumor-infiltrating lymphocytes in breast cancer. J Immunother Cancer 4:59 (2016).
Turcotte et al. Immunotherapy for metastatic solid cancers. Adv Surg 45:341-360 (2011).
U.S. Appl. No. 15/200,751 Office Action dated Feb. 7, 2017.
Valerio et al. Hemorrhagic exanthema due to dengue virus induced by Acetylsalicylic acid. An Sist Sancit Navar 29(3):439-442 (2006).
Van Mierlo et al. Activation of dendritic cells that cross-present tumor-derived antigen licenses CD8+ CTL to cause tumor destruction. J Immunol 173:6753-6759 (2004).
Vaughn et al. Dengue viremia titer, Antibody Response Pattern, and Virus Serotype Correlate with Disease Sensitivity. J Infect Dis 181:2-9 (2000).
Verdijik et al. Limited amounts of DC migrate into the T-cell area of lymph nodes, but have high immune activating potential in melanoma patients. Clin Can Res 15(7):2531-2540 (2009).

(56) References Cited

OTHER PUBLICATIONS

Wahid et al. A comparison of the pattern of liver involvement in Dengue Hemorrhagic Fever with classic Dengue Fever. Southeast Asian J Trop Med Public Health 31(2):259-263 (2000).
Wolchok et al. Guidelines for the evaluation of immune therapy activity in solid tumors: immune-related response criteria. Clin Cancer Res 15(23):7412-7420 (2009).
Wu et al. Human skin Langerhans cells are targets of dengue virus infection. Nature Medicine 6:816-820 (2000).
Yu et al. New Immunotherapy Strategies in Breast Cancer. Int J Environ Res Public Health 14(1):pii:68 (2017).
Zellweger et al. Mouse models to study dengue virus immunology and pathogenesis. Front Imunol 10(5):151 (Apr. 2014).
Zitvogel et al. Therapy of murine tumors with tumor-peptide-pulsed dendritic cells: dependence on T cells, B7 costimulation, and T-helper cell-1 associated cytokines. J Exp Med 183:87-97 (1996).
Zobywalski et al. Generation of clinical grade dendritic cells with capacity to produce biologically active IL-12p70. J Trans! Med 5:18 (2007).
Co-pending U.S. Appl. No. 16/172,487, filed Oct. 26, 2018.
PCT/US2018/037616 International Search Report and Written Opinion dated Nov. 29, 2018.
U.S. Appl. No. 16/172,487 Office Action dated Dec. 14, 2018.
Chiang et al. A dendritic cell vaccine pulsed with autologous hypochlorous acid-oxidized ovarian cancer lysate primes effective broad antitumor immunity: from bench to bedside. Clin Cancer Res 19(17):4801-4815 (2013).
Lövgren et al. Enhanced stimulation of human tumor-specific T cells by dendritic cells matured in the presence of interferon-γ and multiple toll-like receptor agonists. Cancer Immunol Immunother 66(10):1333-1344 (2017).
Paustian et al. Effect of multiple activation stimuli on the generation of Th1-polarizing dendritic cells. Hum Immuon 71(1):24-31 (2011).
Sondak et al. Allogeneic and autologous melanoma vaccines: where have we been and where are we going? Clin Cancer Res 12(7 Pt 2):2337s-2341s (2006).
U.S. Appl. No. 16/413,444 Office Action dated Aug. 19, 2019.
U.S. Appl. No. 16/413,444 Office Action dated Nov. 20, 2019.
Angarone. Epidemiology and Prevention of Viral Infections in Patients with Hematologic Malignancies. Infect Disord Drug Targets 11(1):27-33 (2011).
Anikeeva et al. Mechanisms Controlling-Granule-mediated Cytolytic Activity of Cytotoxic T Lymphocytes. Immunol Res 51(2-3):183-194 (2011).
Dohnal et al. CD40 ligation restores type 1 polarizing capacity in TLR4-activated dendritic cells that have ceased interleukin-12 expression. J Cell Mol Med 13(8B):1741-1750 (2009).
Edelman et al. A live attenuated dengue-1 vaccine candidate (45AZ5) passaged in primary dog kidney cell culture is attenuated and immunogenic for humans. J Infect Dis. 170(6):1448-1455 (1994).
Flavell et al. The polarization of immune cells in the tumour environment by TGFβ. Nat Rev Immunol 10(8):554-567 (2010).
Genevive et al. CD40-CD40 Ligand Interaction between Dendritic Cells and CD8+ T Cells Is Needed to Stimulate Maximal T Cell Responses in the Absence of CD4+ T Cell Help. J Immunol 178(5):2844-2852 (2007).
Jing et al. Combined immune checkpoint protein blockade and low dose whole body irradiation as immunotherapy for myeloma. J ImmunoTher Cancer 3(1):2 (15 pgs) (2015).
Kaka et al. Using Dendritic Cell Maturation and IL-12 Producing Capacity as Markers of Function: A Cautionary Tale. J Immunother 31(4):359-369 (2008).
Kawasaki et al. Toll-Like Receptor Signaling Pathways. Fron Immunol 5:461 (2014).
Lambert et al. Intradermal vaccine delivery: will new delivery systems transform vaccine administration? Vaccine 26:3197-3208 (2008).
Markiewicz et al. IL-12 enhances CTL synapse formation and induces self-reactivity. J Immunol 182(3):1351-1361 (2009).
Media for Multiplitoplasma Viroids Is Not Rare—Causative Agent (available at https://www.alpfmedical.info/causative-agent/i-ptg.html) ALPF Medical Research (5 pgs) (updated Jul. 21, 2017) .
PCT/US2016/040787 International Preliminary Report on Patentability dated Jan. 11, 2018.
PCT/US2016/053554 International Preliminary Report on Patentability dated Apr. 5, 2018.
PCT/US2017/061810 International Search Report and Written Opinion dated Mar. 15, 2018.
PCT/US2017/061810 Invitation to Pay Additional Fees dated Jan. 22, 2018.
PCT/US2018/012408 International Search Report and Written Opinion dated Mar. 29, 2018.
Quatromonie et al. The timing of TGF-β inhibition affects the generation of antigen-specific CD8+ T cells. BMC Immunol 14:30 (2013).
Rigau-Perez et al. Dengue activity in Puerto Rico, 1990. Puerto Rico Health Science Journal 11(2):65-68 (1992).
Santos et al. Dendritic Cell-Based Cancer Vaccines. J Immunol 200(2):443-449 (2018).
Shresta et al. Critical roles for both STAT1-dependent and STAT1-independent pathways in the control of primary dengue virus infection in mice. J Immunol 175:3946-3954 (2005).
U.S. Appl. No. 15/639,632 Office Action dated Aug. 3, 2017.
U.S. Appl. No. 15/799,793 Office Action dated Dec. 13, 2017.
U.S. Appl. No. 15/799,793 Office Action dated May 25, 2018.
Via et al. IL-12 stimulates the development of acute graft-versus-host disease in mice that normally would develop chronic, autoimmune graft-versus-host disease. J Immunol 153(9):4040-4047 (1994).
Yang et al. TGF-beta and immune cells: an important regulatory axis in the tumor microenvironment and progression. Trends Immunol 31(6):220-227 (2010).
Yeo et al. Lack of clinical manifestations in asymptomatic dengue infection is attributed to broad down-regulation and selective up-regulation of host defence response genes. PloS One 9(4):e92240 (2014).

\* cited by examiner

SEQUENCE LISTING

```
<160> NUMBER OF SEQ ID NOS: 7

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Gly Ser Arg Asn Gln Asp Trp Leu
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Ala Tyr Arg Tyr His Leu Leu
1               5
```

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggatcccaag aagggccat                                              20

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggcagctcca tagattgct                                              19

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtgttgctg cagatggaa                                              19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgtcacaga cagtgaggt                                              19

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ile Ile Asn Phe Glu Lys Leu
1               5
```

COMPOSITIONS AND METHODS FOR PRODUCING DENDRITIC CELLS

CROSS-REFERENCE

This application claims the benefit of U.S. Provisional Application No. 62/284,434, filed Sep. 26, 2015, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 22, 1016, is named 48253-703_201_SL.txt and is 1831 bytes in size.

BACKGROUND

Dendritic cells (DCs) are antigen-presenting cells of the immune system. They engulf and process bits of bacteria, viruses, and other pathogens before presenting the relevant protein chain targets (antigenic peptides), to Cytotoxic T Lymphocytes (CTL), which recognize and kill virus-infected or cancer cells, and B-lymphocytes, which make antibodies. DCs also engulf cells which are damaged or dead, and are required to induce either a Type 1 response (activation), a Type 2 response (tolerant), or a Type 0 response (neutral). Because the same 20 amino acids make up body parts (self), as well as pathogens (non-self), DCs must evaluate not only the antigen structure, but also the cytokine and other signaling environment present at the time. This multi-layered system is in place to prevent auto-immunity, where the immune system mistakes self for non-self, as well as allergic responses, where a neutral response is required to maintain balance. This complex system of internal checks and balances is exploited by tumor cells, which arise from "self" cells. Tumor cells often secrete factors such as Transforming Growth Factor-beta (TGFβ) which switch responding immune cells toward a $T_H2$-type tolerant response. This allows the tumor cells to grow unchecked, and often aided by, the immune cells. DCs have the capability of programming $CD4^+$ and $CD8^+$ CTL to recognize the MHC (self-protein ID complex) and associated peptide presented. However, the CTL must then decide whether to ignore the cell as self, or initiate lysis, e.g., through the Fas/FasL or Perforin/Granzyme B cell-death systems. The decision will often rely on the activation state of the CTL, the cytokine environment, and the presence or absence of cell-damage factors, e.g., heat-shock proteins, Toll-like receptor activation signals, and the like. During an active pathogen infection, these systems become activated and help steer the CTL response to a Type 1 attack mode.

Immunotherapy, unlike cytotoxic drugs, radiation, and surgery, stimulates the immune system to recognize and kill tumor cells. Numerous attempts have been made in stimulating the immune system to recognize and destroy tumor cells. These have been met with limited success due to the self-identity of peptides selected as target for immunotherapy, lack of immune activation, adverse events, and/or tumor immune evasion mechanisms.

The ability of current cellular therapies, e.g., dendritic cell therapies, to induce durable, complete responses in advanced cancer patients is low (5-10% in the most immunogenic cancer types, lower in others). Often, dendritic cell therapies produce less than desirable results because of low activation (e.g. not enough immune cells to adequately kill all cancer cells), low targeting (e.g., healthy cells are killed and/or tumor cells are not killed), or an immunosuppressed tumor microenvironment, limiting drug efficacy.

BRIEF SUMMARY

Provided herein are methods for producing primed dendritic cells, comprising: culturing dendritic cells on a hard surface; lysing at least one cell with a hypochlorite solution to produce a lysate; contacting the dendritic cells with the lysate to produce primed dendritic cells; and maturing the primed dendritic cells, wherein maturing comprises contacting the primed dendritic cells with a toll-like receptor 7 agonist or a toll-like receptor 8 agonist. Further provided herein are methods, wherein the primed dendritic cells produce at least 6 ng/mL IL-12p70. Further provided herein are methods, wherein the primed dendritic cells produce at least about 6.5 ng/mL IL-12p70. Further provided herein are methods, wherein the primed dendritic cells produce about 19 ng/mL IL-12p70. Further provided herein are methods, wherein the hard surface is a plastic surface. Further provided herein are methods, wherein the hard surface comprises polystyrene. Further provided herein are methods, wherein the hard surface is substantially free of a component that reduces a Type 1 response produced by the primed dendritic cells. Further provided herein are methods, wherein the component is selected from a fluorinated polyethylene, a fluorinated polypropylene, and a phthalate. Further provided herein are methods, wherein the lysate comprises a plurality of intact cells. Further provided herein are methods, wherein the toll-like receptor 7 agonist or toll-like receptor 8 agonist is an imidazoquinoline compound. Further provided herein are methods, wherein the imidazoquinoline compound is R848. Further provided herein are methods, wherein maturing comprises contacting the primed dendritic cells with (i) a toll-like receptor 2 agonist or a toll-like receptor 4 agonist, or (ii) interferon gamma. Further provided herein are methods, wherein the toll-like receptor 2 agonist or the toll-like receptor 4 agonist is lipopolysaccharide. Further provided herein are methods, wherein maturing further comprises contacting the primed dendritic cells with (i) a toll-like receptor 2 agonist or a toll-like receptor 4 agonist; and (ii) interferon gamma. Further provided herein are methods, wherein maturing comprises contacting the primed dendritic cells with R848; lipopolysaccharide; and interferon gamma. Further provided herein are methods, wherein the at least one cell is a tumor cell. Further provided herein are methods, wherein the dendritic cells are autologous or allogeneic to the subject. Further provided herein are methods, wherein the dendritic cells are allogeneic cells that are HLA matched to the subject. Further provided herein are methods, comprising obtaining the at least one cell from a subject, wherein the cell is associated with a harmful disease state. Further provided herein are methods, wherein the harmful disease state is a proliferative disorder or an autoimmune disorder. Further provided herein are methods, wherein maturing further comprises contacting the primed dendritic cells with (i) a toll-like receptor 2 agonist, a toll-like receptor 4 agonist, or (ii) interferon gamma. Further provided herein are methods, wherein the toll-like receptor 2 agonist or the toll-like receptor 4 agonist is lipopolysaccharide. Further provided herein are methods, wherein maturing further comprises contacting the primed dendritic cells with (i) a toll-like receptor 2 agonist or a toll-like receptor 4 agonist; and (ii) interferon gamma. Further provided herein are methods, wherein maturing comprises contacting the primed dendritic cells with R848;

lipopolysaccharide; and interferon gamma. Further provided herein are methods, wherein a population of the primed dendritic cells has a viability of greater than 70% after freezing and thawing. Further provided herein are methods, wherein a population of the primed dendritic cells has a viability of about 71% to about 79% after freezing and thawing.

Provided herein are methods for producing primed dendritic cells, comprising: culturing dendritic cells on a hard surface; obtaining at least one cancer cell from a subject; lysing the at least one cancer cell with a hypochlorite solution to produce a lysate; contacting the dendritic cells with the lysate to produce primed dendritic cells; and maturing the primed dendritic cells, wherein maturing comprises contacting the primed dendritic cell with a toll-like receptor 7 agonist or a toll-like receptor 8 agonist. Further provided herein are methods, wherein the primed dendritic cells produce at least 6 ng/mL IL-12p70. Further provided herein are methods, wherein the primed dendritic cells produce at least about 6.5 ng/mL IL-12p70. Further provided herein are methods, wherein the primed dendritic cells produce about 19 ng/mL IL-12p70. Further provided herein are methods, wherein the hard surface is a plastic surface. Further provided herein are methods, wherein the hard surface comprises polystyrene. Further provided herein are methods, wherein the hard surface is substantially free of a component that reduces a Type 1 response produced by the primed dendritic cells. Further provided herein are methods, wherein the component is selected from a fluorinated polyethylene, a fluorinated polypropylene, and a phthalate. Further provided herein are methods, wherein the lysate comprises a plurality of intact cells. Further provided herein are methods, wherein the plurality of intact cells is a plurality of proliferation-inactivated cancer cells. Further provided herein are methods, wherein the toll-like receptor 7 agonist or toll-like receptor 8 agonist is an imidazoquinoline compound. Further provided herein are methods, wherein the imidazoquinoline compound is R848. Further provided herein are methods, wherein the toll-like receptor 2 agonist or a toll-like receptor 4 agonist is lipopolysaccharide. Further provided herein are methods, wherein the dendritic cells are autologous or allogeneic to the subject. Further provided herein are methods, wherein the dendritic cells are allogeneic cells that are HLA matched to the subject. Further provided herein are methods, wherein maturing further comprises contacting the primed dendritic cells a toll-like receptor 2 agonist, a toll-like receptor 4 agonist, interferon gamma, or combinations thereof.

Provided herein are methods for treatment or reduction of a cancer in a subject in need thereof, comprising: culturing dendritic cells on a hard surface; obtaining at least one cancer cell; lysing the at least one cancer cell with a hypochlorite solution to produce a lysate; contacting the dendritic cells with the lysate, thereby generating primed dendritic cells; and administering the primed dendritic cells to a subject in need thereof. Further provided herein are methods, wherein the primed dendritic cells produce at least about 6 ng/mL IL-12p70. Further provided herein are methods, wherein the primed dendritic cells produce at least about 6.5 ng/mL IL-12p70. Further provided herein are methods, wherein the primed dendritic cells produce about 19 ng/mL IL-12p70. Further provided herein are methods, wherein the primed dendritic cells produce 19 ng/mL IL-12p70. Further provided herein are methods, wherein the primed dendritic cells produce about 15 ng/mL IL-12p70 to about 23 ng/mL IL-12p70. Further provided herein are methods, wherein the primed dendritic cells produce 15 ng/mL IL-12p70 to 23 ng/mL IL-12p70. Further provided herein are methods, wherein the dendritic cells are autologous or allogenic to the subject. Further provided herein are methods, wherein the at least one cancer cell is from the subject. Further provided herein are methods, comprising maturing the primed dendritic cells, wherein maturing comprises adding a maturation reagent, wherein the maturation reagent comprises a toll-like receptor 7 agonist or a toll-like receptor 8 agonist. Further provided herein are methods, wherein maturing further comprises contacting the primed dendritic cells with (i) a toll-like receptor 2 agonist or a toll-like receptor 4 agonist; or (ii) interferon gamma. Further provided herein are methods, wherein the toll-like receptor 2 agonist or the toll-like receptor 4 agonist is lipopolysaccharide. Further provided herein are methods, wherein maturing further comprises contacting the primed dendritic cells with (i) a toll-like receptor 2 agonist or a toll-like receptor 4 agonist; and (ii) interferon gamma. Further provided herein are methods, wherein maturing comprises contacting the primed dendritic cells with R848; lipopolysaccharide; and interferon gamma.

Provided herein are methods for treatment or reduction of cancer in a subject in need thereof, comprising: obtaining dendritic cells from a subject; culturing the dendritic cells on a hard surface; obtaining a cancer cell from the subject; lysing the cancer cell with a hypochlorite solution to produce a lysate; contacting the dendritic cells with the lysate, thereby generating primed dendritic cells; administering the primed DCs to the subject; and administering a Dengue virus to the subject in need thereof. Further provided herein are methods, wherein the Dengue virus is DENV-2 strain #1710. Further provided herein are methods, wherein the hard surface is a hard plastic surface. Further provided herein are methods, wherein the hard plastic surface is a polystyrene surface. Further provided herein are methods, wherein the primed dendritic cells produce at least 6 ng/mL IL-12p70. Further provided herein are methods, wherein the primed dendritic cells produce at least about 6.5 ng/mL IL-12p70. Further provided herein are methods, wherein the primed dendritic cells produce about 19 ng/mL IL-12p70. Further provided herein are methods, wherein the primed dendritic cells produce about 6.5 to 23 ng/mL IL-12p70.

Provided herein are methods for clearing cancer cells in a subject, comprising: administering a Dengue virus serotype 2 to a subject in need thereof; priming a dendritic cells, wherein priming comprises: exposing the dendritic cells to a lysate to produce primed dendritic cells, wherein the lysate comprises a plurality of cancer cells, each cancer cell comprising an antigen present on the surface of said cancer cell; and administering the primed dendritic cells to the subject, wherein the administration provides for clearance of 33% or more of a cancer cell population in the subject. Further provided herein are methods wherein the administration provides for clearance of 33% of the cancer cell population in the subject. Further provided herein are methods, further comprising intravenously administering the Dengue virus serotype 2 and intravenously administering the population of primed dendritic cells. Further provided herein are methods, wherein the plurality of cancer cells is from the subject. Further provided herein are methods, wherein the Dengue virus serotype 2 is DENV-2 strain #1710.

Provided herein are methods for treating or reducing cancer in a subject in need thereof, comprising administering the primed dendritic cells produced by a method comprising: culturing dendritic cells on a hard surface; lysing at least one cell with a hypochlorite solution to produce a lysate; contacting the dendritic cells with the lysate to produce primed dendritic cells; and maturing the primed dendritic cells, wherein maturing comprises contacting the primed dendritic cell with a toll-like receptor 7 agonist or a toll-like receptor 8 agonist. Further provided herein are methods, wherein the primed dendritic cells are administered intravenously. Further provided herein are methods, comprising administering Dengue Virus 2 to the subject. Further provided herein are methods, wherein the Dengue Virus 2 is strain #1710.

Provided herein are primed dendritic cells produced by a method comprising: culturing dendritic cells on a hard surface; lysing at least one cell with a hypochlorite solution to produce a lysate; contacting the dendritic cells with the lysate to produce primed dendritic cells; and maturing the primed dendritic cells, wherein maturing comprises contacting the primed dendritic cell with a toll-like receptor 7 agonist or a toll-like receptor 8 agonist. Further provided herein are cells, wherein the primed dendritic cell is used for treatment of a cancer.

Provided herein are uses of the primed dendritic cells prepared by a method comprising: culturing dendritic cells on a hard surface; lysing at least one cell with a hypochlorite solution to produce a lysate; contacting the dendritic cells with the lysate to produce primed dendritic cells; and maturing the primed dendritic cells, wherein maturing comprises contacting the primed dendritic cell with a toll-like receptor 7 agonist or a toll-like receptor 8 agonist, for treating cancer.

Provided herein are effective amounts of the primed dendritic cells prepared by a method comprising: culturing dendritic cells on a hard surface; lysing at least one cell with a hypochlorite solution to produce a lysate; contacting the dendritic cells with the lysate to produce primed dendritic cells; and maturing the primed dendritic cells, wherein maturing comprises contacting the primed dendritic cell with a toll-like receptor 7 agonist or a toll-like receptor 8 agonist, for use in treating cancer.

BRIEF DESCRIPTION OF THE FIGURES

FIG. 1 depicts an exemplary method of treatment with Dengue virus and primed dendritic cells.

FIG. 2 exemplifies a method of treatment with Dengue virus and primed dendritic cells schedule for treatment with Dengue virus and primed dendritic cells FIG. 3 shows a plot of corresponding to the number of lung metastases from melanoma cells in mice under various treatment conditions. The patterned bars represent the mean number of lung metastases for each condition.

FIG. 4 shows a plot of corresponding to the number of lung metastases from melanoma cells in mice under various treatment conditions. The patterned bars represent the mean number of lung metastases for each condition.

FIG. 5 shows a plot of flow cytometry data confirming isolation of CD14+ monocytes.

FIG. 6 shows a chart representing protein expression of IL-12p70 by DCs produced by methods disclosed herein relative to that of DCs produced by several comparator methods.

DETAILED DESCRIPTION

Provided herein are methods for preparation of primed dendritic cells (DCs). Further provided herein are methods for exposing the primed dendritic cells to antigens associated with a disease state, e.g., tumor antigens, resulting primed dendritic cells capable of inducing specific and robust responses from cytotoxic T lymphocyte (CTL) toward cancer cells. Further provided herein are methods for administering such DCs into a subject for treatment of a disorder linked to the disease state. In some instances, the disorder is cancer. In some instances, the disorder is an autoimmune disorder, e.g., rheumatoid arthritis and multiple sclerosis. In some instances, the disorder is a human immunodeficiency virus (HIV) infection or an acquired immunodeficiency syndrome. In some instances, the subject is administered a Dengue Virus prior to administration of the primed DCs.

Priming the dendritic cells generally involves contacting the dendritic cells with one or more tumor antigens that are present on target cancer cells. In some cases, the dendritic cells are primed with the tumor antigen alone, the tumor antigen having been synthesized, isolated or purified. Alternatively or additionally, the dendritic cells are primed with a tumor cell lysate, wherein the tumor cell lysate contains the tumor antigen. In some cases, the dendritic cell is primed with a whole cancer cell expressing the tumor antigen. The dendritic cell is then administered to the subject, where it will present the tumor antigen to the CTL, and thus, tailor the CTL for recognition and destruction of target cancer cells.

Provided herein are methods which limit dendritic cells exposure to polymers contained in plastic container material. For example, in the case of soft plastic bags, polymers may leach into the media solution and impact DC activity. Instead, dendritic cells may be cultured, stored and shipped in and on a hard container, such as a polystyrene tissue culture plate. This avoids a reduction in dendritic cell immunostimulatory activity that can be caused by exposure to polymers contained in soft plastic bags. For example, these polymers can reduce the amount of IL-12 produced by the dendritic cells, thereby reducing their capacity to induce a robust CTL response. Examples provided herein demonstrate that primed dendritic cells generated by the methods disclosed herein are capable of secreting at least 18 pg/mL of IL-12p70, whereas dendritic cells produced by standard methods typically only produce 4-6 pg/mL of IL-12p70.

In some cases, it is desirable or advantageous to prime the dendritic cells with a tumor lysate. Notably, the methods disclosed herein utilize a gentle cell lysis protocol that preserves the integrity of the tumor antigen. This gentle lysis may be achieved by exposing the tumor or cancer cells to a calcium or sodium hypochlorite solution for no more than about 30-60 minutes. Similarly, any tumor cells used to prime dendritic cells are disassociated gently, for instance, by a Miltenyi GentleMACS system, or the like.

Primed dendritic cells prepared by the methods disclosed herein may be administered to the subject along with an agent that will boost the subject's immune system. For example, the primed dendritic cells may be administered to the subject after infecting the subject with a virus. By way of example, the methods and examples disclosed herein use a Dengue virus, particularly Dengue virus serotype 2 strain #1710, which is relatively safe (e.g., no known occurrence of lethality or serious adverse events). This virus provides for the activation of a suppressed immune system (e.g., by producing a $T_H1$ polarity shift), and improving targeting specificity, thereby providing higher efficacy and safety relative to current cellular therapies. The combination of primed dendritic cells with a viral infection provides for an effective treatment with minimal administration, possibly as few as one time, which avoids the challenge of subject adherence to therapy. The primed dendritic cells may be autologous, meaning derived from a subject's own cells, or allogenic, derived from another subject with a similar tissue type.

DEFINITIONS

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The term "subject" as used herein includes to mammals. Mammals include rats, mice, non-human primates, and primates, including humans.
Methods of Isolating and Priming Dendritic Cells (DC)

Provided herein are methods for priming DCs and administering the primed DCs to a subject in need thereof, wherein the DC induce a response from cytotoxic T lymphocytes (CTL) resulting in cytotoxicity of target cells. The DCs may comprise allogeneic dendritic cells or autologous dendritic cells. In some instances, the methods described herein comprise administering allogeneic primed dendritic cells to a subject. In some instances, the methods described herein comprise administering autologous primed dendritic cells to a subject. The methods disclosed herein comprising administering primed DCs to the subject may be referred to herein as "dendritic cell vaccination."

In some instances, methods described herein comprise obtaining dendritic cells from $CD34^+$ progenitor cells in the bone marrow. In some instances, methods described herein comprise obtaining dendritic cells from $CD1^+ CD14^+$ immature monocytes in the peripheral blood. In some instances, obtaining the dendritic cells comprises leukapheresis. In some instances, leukapheresis comprises withdrawing a unit of blood from the subject or a donor, separating a series of blood-components: red cells, platelets, and most of the plasma factors, which are returned to the subject, with the white blood cells remaining. In some instances, methods described herein comprise assessing the white blood cells for sterility, shipping or storing them cold (4° C.), and or processing the DCs from the apheresis product.

Methods of DCs production disclosed herein may comprise separating monocytes in the unit of blood from other white cells, including, but not limited to, T cells, B cells, NK cells, Eosinophils and Basophils. This may be accomplished with immuno-magnetic selection or by adherence properties. Immuno-magnetic selection involves contacting white blood cells from the unit of blood with a sterile plastic column with plastic beads coated with antibodies for immune cells, such as, by way of non-limiting example, CD surface proteins: (CD4, CD8, CD56, etc.). Unwanted (non-monocyte) cells will adhere to the beads, leaving the monocytes to pass through and be collected. In positive selection, magnetic beads may be coated with antibodies for CD1 and/or CD14 to capture monocytes, a magnet is placed against the column, and unwanted cells are flushed out of the column with a buffered saline solution or cell-viable media. The monocytes are then washed off the beads and collected in a following step. In adherence selection, the properties of monocytes to stick to certain surfaces are used to separate them by running the apheresis product down a slanted column.

Provided herein are methods for cell collection which may comprise collecting only a few thousand monocytes from the unit of blood. Effective immunotherapy generally requires DC doses in the range of 50 million. Thus, methods disclosed herein may comprise expanding monocytes, as well as any precursors thereof, and any cells differentiated therefrom (e.g., DCs). Expanding cells may comprise contacting cells with factors such as growth factors, colony-stimulation factors, cytokines, or any other proliferation or growth inducing factors, and combinations thereof. By way of non-limiting example, the recombinant human growth factors rhuInterleukin-4 (IL-4), and rhuGranulocyte-Macrophage-Colony-Stimulation Factor (GM-CSF), may be used to accomplish the expansion of DC numbers. In addition, IL-4 and GM-CSF may be required to develop mature DCs from monocytes, which have poor antigen-uptake and CTL-stimulating ability, compared to mature DCs. Thus, IL-4 and GM-CSF may expand the number and the development of mature-DC markers. DC markers may include, but are not limited to CD11, CD80, and CD83, as well as increased expression of both Class I (for presentation of short peptides to $CD8^+$ cells), and Class II (for presentation of longer peptides to $CD4^+$ Helper-Inducer T lymphocytes) MHC complexes. Expanding cells may produce mature D DCs C in the tens of millions within about 2 days. Expanding cells may produce mature DCs in the tens of millions within about 3 days. Expanding cells may produce mature DCs in the tens of millions within about 4 days. Expanding cells may produce mature DCs in the tens of millions within about 5 days. Expanding cells may produce mature DCs in the tens of millions within about one week.

In some instances, methods described herein comprise contacting or pulsing DCs with peptides/antigens, tumor cells, tumor supporting cells, tumor cell lysate and/or tumor supporting cell lysate. The term "pulsing," as used herein, generally refers to contacting the cells more than once at one or more intervals, and may be used interchangeably with contacting, unless specified otherwise. In some instances, the methods comprise contacting or pulsing DCs with a peptide that binds MHC Class I molecules ("MHC Class I peptide"). In some instances, methods described herein comprise contacting or pulsing DC with a peptide that binds MHC Class II molecules ("MHC Class II peptides"). In some instances, methods described herein comprise contacting or pulsing DC with MHC Class I peptides and MHC Class II peptides. In some instances, the contacting or pulsing makes the DCs competent to prime CTL and target CTL to tumors. In some instances, methods described here comprise contacting or pulsing DC with manufactured/synthetic Class I and/or Class II peptides. In some instances, the Class I and/or class II peptides are manufactured, then added to the DC medium, optionally in in microgram quantities or less. In some instances, methods described herein include Class II peptides for a sustained immune response. In some instances, methods described herein comprise DNA or RNA sequencing of the peptide (i.e. tumor antigen) and/or using electroporation to insert the DNA or RNA into the DCs to trigger antigen processing. In some instances, methods described herein do not require HLA matching of DCs. In some instances, the peptide or portion thereof is represented by an amino acid sequence selected from EGSRNQDWL (SEQ ID NO:1), (TAYRYHLL) (SEQ ID NO: 2), or combinations thereof.

Class I peptides may by manufactured, then added to the DC medium in microgram quantities. However, this technique is costly, because the peptides must be matched to the subject's HLA type, and if the tumor cell does not present that antigen, it can evade detection and lysis. The lack of Class II peptides to activate $CD4^+$ help leads to rapid decline of immune response power. Other methods may comprise RNA sequencing of common tumor antigens, then using electroporation to insert the RNA into the DCs to trigger antigen processing. This method does not require HLA matching, and includes Class II peptides for a sustained immune response. However, RNA sequencing may be technically complex, and may only present a limited number of antigens of thousands of potential gene products. For these reasons, autologous whole-tumor cells or their lysate have the advantages of low cost, ready availability by biopsy (1-2 gm sufficient), and contain the full array of potential antigens for a broad and deep immune response.

Methods for dendritic cell priming described herein may comprise obtaining whole tumor cells and/or lysates thereof. Tumor cells may be killed by radiation or other means and preparing lysate by various methods. In some instances, lysing the tumor cells does not comprise trypsin enzyme digestion and freeze-thaw cycles, which are simple and fast, but can damage the delicate peptides within. The methods disclosed herein may employ an automated cell processor (e.g. the Miltenyi GentleMACS system), which allows the sample to be manually minced, suspended in PBS solution, then a pre-selected tissue-specific software-controlled rotor system separates the tumor cells. The single-cell suspension may be membrane-lysed with minimal damage to tumor peptides.

Methods for dendritic cell priming described herein may comprise contacting the dendritic cells with autologous tumor cells or lysates thereof. In some instances, methods described herein comprise contacting the dendritic cells with autologous whole-tumor cells (e.g. tumor cells and tumor supporting cells) or lysates thereof which contain the full array of potential antigens for a broad and deep immune response. Methods for dendritic cell priming described herein may comprise contacting the dendritic cells with tumor cell lysate comprising apoptotic or necrotic bodies. In further instances, the tumor cell lysate comprises tumor antigens from the microenvironment surrounding the tumor cells, such as extracellular matrix proteins.

Methods for dendritic cell priming described herein may comprise contacting the DCs with an augmenting agent that will augment the priming, proliferation or viability of the DCs. By way of non-limiting example, the augmenting agent may be selected from lymphokines, monokines, cytokines, growth factors, cells, cell fragments, (non-protein) small molecules, antibodies, antibody fragments, nucleic acids, and combinations thereof.

Methods for preparing cells and antigens for DC priming may comprise rendering the target cells (e.g., cancer cells) incapable of cell division. For example, the methods may comprise treating cells with mytomycin C or radiation to render cells incapable of cell division. These may include cells that are added as augmenting agents or cells used to pulse DCs (e.g., tumor cells).

In some instances, methods described herein comprise pulsing the DCs from about 1 hour to about 24 hours. In some instances, methods described herein comprise pulsing the DCs from about 12 hours to about 48 hours. In some instances, methods described herein comprise pulsing the DCs from about 8 hours to about 24 hours. In some instances, methods described herein comprise pulsing the DCs for about 18 hours. Pulsing may comprise contacting the DCs at least once with the peptides/antigens, tumor cells, tumor supporting cells, tumor cell lysate and/or tumor supporting cell lysate. Pulsing may comprise contacting the DCs at least twice with the peptides/antigens, tumor cells, tumor supporting cells, tumor cell lysate and/or tumor supporting cell lysate. Pulsing may comprise contacting the DCs at least three times with the peptides/antigens, tumor cells, tumor supporting cells, tumor cell lysate and/or tumor supporting cell lysate. Pulsing may comprise contacting the DCs less than two times, less than three times, less than four times, less than five times, or less than 10 times with the peptides/antigens, tumor cells, tumor supporting cells, tumor cell lysate and/or tumor supporting cell lysate. Pulsing may comprise adding the peptides/antigens, tumor cells, tumor supporting cells, tumor cell lysate and/or tumor supporting cell lysate to the DC more than once, such that the peptides/antigens, tumor cells, tumor supporting cells, tumor cell lysate and/or tumor supporting cell lysate accumulates in the DC culture media. Pulsing may comprise washing the cells or removing the DC culture media between one or more pulses.

Methods described herein may comprise contacting DC with a maturing agent to enhance, complete or finalize the maturation of the DC. IN some embodiments, the maturing agent also acts as a "danger signal." Without this danger signal, the tumor antigen may induce $T^{reg}$ production or activity, which will ultimately lower CTL activity. In some embodiments, the maturing agent/danger signal is an inflammatory signal. The inflammatory signal may also be referred to as an inflammatory mediator. Inflammatory mediators may include cytokines, as well as other factors (e.g., chemokines, adhesion molecules, etc.), that may not be classified by those in the art as cytokines, but affect inflammation either directly or indirectly, In some embodiments, the inflammatory mediator is selected from a chemokine, a cytokine, a pathogen, a non-peptidic small molecule, a compound, an antibody, a peptide, fragments thereof, portions thereof, and combinations thereof. In some embodiments, the inflammatory signal is a modulator of a pattern recognition receptor (PRR) or pathway thereof.

In some embodiments, inflammatory signals are selected from an interferon, a toll-like receptor signaling modulator, and combinations thereof. By way of non-limiting example, the interferon may be interferon-gamma. In some embodiments, the inflammatory signal is a toll-like receptor signaling pathway modulator.

In some embodiments, the inflammatory signal is a toll-like receptor (TLR) signaling pathway regulator. By way of non-limiting example, the toll-like receptor signaling pathway regulator may be lipopolysaccharide (LPS), a polysaccharide from bacterial cell walls.

The toll-like receptor signaling pathway regulator may be selected from a toll-like receptor signaling pathway regulator that regulates TLR1, TLR2, TLR3, TLR4, TLR5, TLR6, TLR7, TLR8, TLR9 and TLR 10. The toll-like receptor signaling pathway regulator may be a ligand, a binding protein, an antibody, an agonist or an antagonist, of a TLR. The toll-like receptor signaling pathway regulator may be selected from a peptide, a protein, a cell fragment, a cell-wall component, a lipoprotein, a peptidoglycan, a polysaccharide, a monosaccharide, and a small molecule compound. The toll-like receptor signaling pathway regulator may be a portion of an animal cell, a plant cell, a bacterial cell, a yeast cell, a fungal cell, and combinations thereof. The toll-like receptor signaling pathway regulator may be a TLR2 signaling pathway regulator. By way of non-limiting example, the TLR2 signaling pathway regulator may be lipoteichoic acid, MALP-2, MALP-4, OspA, Porin, LcrV, lipomannan, GPI anchor, lysophosphatidylserine, lipophosphoglycan, glycophosphatidylinositol, zymosan, hsp60, and hemagglutinin. The toll-like receptor signaling pathway regulator may be a TLR4 signaling pathway regulator. By way of non-limiting example, the TLR4 signaling pathway regulator may be buprenorphine, carbamazepine, ethanol, fentanyl, levorphanol, LPS, methadone, morphine, oxcarbazepine, oxycodone, pethidine, and glucuronoxylomannan. The toll-like receptor signaling pathway regulator may be a TLR7 signaling pathway regulator. By way of non-limiting example, the TLR7 signaling pathway regulator may be a single stranded RNA or an imidazoquinoline compound. The toll-like receptor signaling pathway regulator may be a TLR8 signaling pathway regulator. By way of non-limiting example, the TLR8 signaling pathway regulator may be a single stranded RNA, a G-rich oligonucleotide or an imidazoquinoline compound. The imidazolquinoline compound may be R848.

After exposure to the inflammatory signal, the DC may up-regulate their CD80/CD83$^+$ activation markers, increase production of IL-12p70 to induce a Type 1 CTL response, and become resistant to further antigen uptake and processing.

Methods for producing primed dendritic cells described herein may comprise contacting primed dendritic cells with interferon gamma. In some embodiments, the methods comprise culturing the primed dendritic cells in a culture media with a concentration of interferon gamma selected from about 100 U/mL to about 10,000 U/mL, about 500 U/mL to about 5000 U/mL, and about 500 U/mL to about 2,000 U/mL. In some embodiments, the methods comprise culturing the primed dendritic cells in a culture media with a concentration of interferon gamma of about 500 U/mL. In some embodiments, the methods comprise culturing the primed dendritic cells in a culture media with a concentration of interferon gamma of about 1000 U/mL. In some embodiments, the methods comprise culturing the primed dendritic cells in a culture media with a concentration of interferon gamma of about 2000 U/mL.

Methods for producing primed dendritic cells described herein may comprise contacting primed dendritic cells with TLR8 agonist R848. In some embodiments, the methods comprise culturing the primed dendritic cells in a culture media with a concentration of R848 selected from about 0.1 µg/mL to about 50 µg/mL, about 1 µg/mL to about 20 µg/mL, and about 1 µg/mL to about 10 µg/mL. In some embodiments, the methods comprise culturing the primed dendritic cells in a culture media with a concentration of R848 of about 1 µg/mL. In some embodiments, the methods comprise culturing the primed dendritic cells in a culture media with a concentration of R848 of about 5 µg/mL. In some embodiments, the methods comprise culturing the primed dendritic cells in a culture media with a concentration of R848 of about 10 µg/mL.

Methods for producing primed dendritic cells described herein may comprise contacting primed dendritic cells with lipopolysaccharide. In some embodiments, the methods comprise culturing the primed dendritic cells in a culture media with a concentration of lipopolysaccharide selected from about 1 ng/mL to about 100 ng/mL, about 1 ng/mL to about 50 ng/mL, and about 1 ng/mL to about 25 ng/mL. In some embodiments, the methods comprise culturing the primed dendritic cells in a culture media with a concentration of lipopolysaccharide of about 5 ng/mL. In some embodiments, the methods comprise culturing the primed dendritic cells in a culture media with a concentration of lipopolysaccharide of about 10 ng/mL. In some embodiments, the methods comprise culturing the primed dendritic cells in a culture media with a concentration of lipopolysaccharide of about 15 ng/mL.

Methods described herein may comprise sterility, specificity, and viability assessment of the DCs. The testing may occur before shipping or storing the DCs. The testing may occur after shipping or storing the DCs. The methods may comprise measuring expression level of IL-12p70 in DCs, either at the RNA or protein level. IL-12p70 is an independent predictor of clinical response, tested across numerous trials in the last two decades, some with about 40% response rates. The expression level of IL-12p70 in primed DCs produced by the methods disclosed herein may be at least about two times greater than primed DCs produced/stored/shipped by traditional methods. The expression level of IL-12p70 in primed DCs produced by the methods disclosed herein may be at least about two times greater than primed DCs produced/stored/shipped by traditional methods ("traditional primed DC"). The expression level of IL-12p70 in primed DCs may be at least about 10%, at least about 20%, at least about 30%, at least about 40%, at least about 50%, at least about 60%, at least about 70%, at least about 80%, at least about 90%, or at least about 100% greater than traditional primed DCs. The expression level of IL-12p70 in primed DCs may be at least about three times greater than traditional primed DCs. The expression level of IL-12p70 in primed DCs may be at least about four times greater than traditional primed DCs. The expression level of IL-12p70 in primed DCs produced by the methods disclosed herein may be about two to about twenty times greater than traditional primed DCs.

Provided herein are dendritic cells that produce more than 6 ng/mL of IL-12p70. Also provided herein are dendritic cells that produce more than 10 ng/mL of IL-12p70. In some instances, DCs produced by methods described herein produce at least about 10 ng/mL, at least about 12 ng/mL, at least about 14 ng/mL, at least about 16 ng/mL, at least about 18 ng/mL, at least about 20 ng/mL, at least about 22 ng/mL, or at least about 24 ng/mL. In some instances, DCs produced by methods described herein produce about 10 ng/mL to about 30 ng/mL. In some instances, DCs produced by methods described herein produce from about 10 ng/mL to about 25 ng/mL. In some instances, DCs produced by methods described herein produce from about 15 ng/mL to at least about 23 ng/mL. In some instances, DCs produced by methods described herein produce from about 6.5 ng/mL to at least about 23 ng/mL.

CTL Response

Methods for producing DCs described herein may comprise testing the ability of the DCs to induce a CTL response. Measuring the level of the CTL response may comprise measuring cytokines or inflammatory mediators in blood, serum or plasma from the subject. Measuring the level of the CTL response may comprise measuring a change in the level of a cytokine or inflammatory mediator in blood, serum or plasma from the subject. Measuring the level of the CTL response may comprise measuring the production of a cytokine or inflammatory mediator in vitro. Cytokines and inflammatory mediators may include interleukins, migration inhibitory proteins, monocyte chemotactic proteins, monocyte chemoattractant proteins, interferons, tumor necrosis factors, colony stimulating factors (CSFs), macrophage inflammatory proteins, monokines, chemokines, chemokine ligands (CCLs), and C-X-C motif chemokines (CXCL), and receptors thereof. Cytokines and inflammatory mediators include, but are certainly not limited to, interleukin 1 beta (IL-1b), interleukin 2 (IL-2), interleukin 4 (IL-4), interleukin 5 (IL-5), interleukin 7 (IL-7), interleukin 8 (IL-5), interleukin 10 (IL-10), interleukin 13 (IL-13), interleukin 6 (IL-6), interleukin 12 (IL-12), interleukin 15 (IL-15), interleukin 17 (IL-17), Rantes, Eotaxin, macrophage inflammatory protein 1 alpha (MIP-1a), macrophage inflammatory protein 1 beta (MIP-1b), granulocyte macrophage colony-stimulating factor (GM-CSF), monocyte chemoattractant protein-1 (MCP-1), interferon alpha (IFNa), interferon gamma (IFNg), interleukin 1 receptor alpha (IL-1Ra), interleukin 2 receptor (IL-2R), tumor necrosis factor alpha (TNFa), interferon gamma induced protein (IP-10), and monokine induced by gamma interferon (MIG). CTL response may be measured by expression of tumor response genes (MxA, etc.), enabling high cancer killing (turning "cold" tumors "hot"), and generating further tumor shrinkage in non-responder or low responders.

Hard Surface

Methods for DC preparation described herein may comprise culturing DCs on a hard surface. The term, "hard surface," as used herein, generally refers to a standard plastic tissue culture plate or flask (e.g. a polystyrene plate). The methods disclosed herein comprise culturing DCs on a hard surface to which the DCs can adhere. In some embodiments, the hard surface is coated with a protein, peptide, extracellular matrix molecule, polymer, or combinations thereof. In some embodiments, the hard surface is not coated (e.g., the DCs adhere directly to the hard plastic surface). The hard surface is contrasted to a soft tissue culture bag, also known as cell differentiation bags. Soft tissue culture bags may be bags comprising polymers or chemicals (e.g. phthalates) that reduce the DC's Type 1 response capability. Soft tissue culture bags may be bags comprising polymers or chemicals that evoke a neutral Type 0 response from the DCs, rendering the DCs functionally inert. Soft tissue culture bags may be bags comprising a polymer selected from polyethylene, fluorinated ethylene propylene (FEP), hexafluoropropylene, tetrafluoroethylene, polytetrafluoroethylene, and co-polymers thereof, and combinations thereof.

Methods for DC preparation described herein may comprise transferring the DCs to a storage unit. The storage unit may also be a shipping unit. The storage unit may be selected from a flexible or soft container or surface (e.g., a bag) or a hard container or surface (e.g., a flask or plate). The storage unit may comprise a hard plastic surface. The storage unit may consist essentially of a hard plastic surface. The storage unit may consist of a hard plastic surface. The storage unit may comprise a non-plastic surface (e.g., glass). The storage unit may consist essentially of a non-plastic surface. The storage unit may consist of a non-plastic surface. The storage unit may be free of any polymers that would be taken up by, and/or induce a response in, cells stored within the storage unit. The storage unit may be free or essentially free of polymers that induce a neutral or Type 0 response in immature DCs. A neutral response may be characterized by low expression of IL-12p70. The storage unit may be essentially free of any polymers that would be taken up by, and/or induce a response in, cells stored within the storage unit. Essentially free may mean that the storage unit is at least 90%, at least 95%, at least 98%, or at least 99% free of any polymers that would be taken up by, and/or induce a response in, cells stored within the storage unit. Essentially free may mean that the storage unit is at least 99.5%, at least 99.6%, at least 99.7%, at least 99.8%, or at least 99.9% free of any polymers that would be taken up by, and/or induce a response in, cells stored within the storage unit.

Provided herein are storage units for storing DCs produced by methods described herein, wherein the storage units comprise an inner surface, wherein the inner surface is the surface of the storage unit that is in contact with cells stored therein. The inner surface may consist of a hard plastic surface. The inner surface may be glass. The inner surface may be absent of any polymers that would be taken up by, and/or induce a response in, cells stored within the storage unit. The inner surface may be constructed of polymers that are not taken up by immature DC or any cells stored within the storage unit. The inner surface may be free of any polymers that would be taken up by, and/or induce a response in, cells stored within the storage unit. The inner surface may be essentially free of any polymers that would be taken up by, and/or induce a response in, cells stored within the storage unit. The inner surface may be at least 90%, at least 95%, at least 98%, or at least 99% free of any polymers that would be taken up by, and/or induce a response in, cells stored within the storage unit following addition of cells and storage media. The inner surface may be at least 99.5%, at least 99.6%, at least 99.7%, at least 99.8%, or at least 99.9% free of any polymers that would be taken up by, and/or induce a response in, cells stored within the storage unit following addition of cells and storage media. The inner surface may be free or essentially free of polymers that induce a neutral or Type 0 response in immature DCs. A neutral response may be characterized by low expression of IL-12p70.

Provided herein are storage units for storing DCs produced by methods described herein, wherein the storage units are suitable for freezing at −70° C. in liquid $N_2$, storage up to 1 year, and shipping to the clinic for use. The methods may comprise storing and/or shipping mature DCs, immature DCs, monocytes or blood in a storage unit. The methods may comprise shipping cells cool overnight. The methods may comprise thawing or warming cells to 37° C. (e.g., in a warm-water bath).

Methods of Isolating and Lysing Tumor Cells

Provided herein are methods for treating a subject, comprising administering the DCs disclosed herein to target tumor cells. In some instances, DCs are primed with tumor cells from a subject. In some instances, the tumor cells are isolated cells from a tumor microenvironment of the subject, referred to herein as tumor supporting cells. In some instances, dendritic cells are exposed to/pulsed with tumor cells, tumor supporting cells and/or peptides thereof, such that the dendritic cells will target tumor cells and/or tumor supporting cells that support tumor growth and metastasis (e.g. endothelial cells, vascular cells, immune cells, etc.). In some instances, peptides/antigens from tumor cells and tumor supporting cells induce dendritic cells or cytotoxic lymphocytes with receptors for peptides/antigens on both tumor cells and tumor supporting cells, resulting in targeting of the dendritic cells or cytotoxic lymphocytes to the tumor microenvironment rather than only the tumor cells. In some instances, tumor cells and/or tumor supporting cells are obtained from a biopsy of tumor tissue. In some instances, the biopsy comprises cells selected from tumor cells, adipocytes, fibroblasts, endothelial cells, infiltrating immune cells, and combinations thereof. In some embodiments, the methods comprise expanding tumor cells in order to have a sufficient number of tumor cells, tumor cell lysates or tumor cell antigens to effectively and optimally prime/pulse the DC. Expanding may comprise proliferating of the tumor cells in vitro.

Provided herein are methods for activating DCs disclosed herein to target tumor cells, wherein the DCs are activated with lysed tumor cells and/or tumor supporting cells and surrounding extracellular matrix. In some instances, lysing comprises contacting the tumor cells and/or tumor supporting cells with an $NH_4Cl$ enzyme solution to eliminate red blood cells. In some instances, the lysing comprises contacting the tumor cells and/or tumor supporting cells with hypochlorous acid solution to induce immunogenic cell death. In some instances, the cells are lysed gently enough to not destroy peptides. In some instances, the cells are lysed to produce apoptotic or necrotic bodies. In some instances, the methods comprise lysing the tumor cells and/or tumor supporting cells with an enzymatic solution. In some instances, the methods comprise lysing the tumor cells and/or tumor supporting cells with a peroxide-free solution or a low peroxide-containing solution.

Provided herein are methods for activating DCs disclosed herein comprising lysing the tumor cells with a hypochlorite solution (HOCL). In some instances, the hypochlorite solution comprises sodium chlorite. In some instances, the hypochlorite solution comprises calcium chlorite. In some instances, the concentration of the hypochlorite in a media in which the tumor cells are suspended is about 10 µM, about 20 µM, about 30 µM, about 40 µM, about 50 µM, about 60 µM, about 70 µM, about 80 µM, about 90 µM, or about 100 µM.

Provided herein are methods for methods activating DCs comprise lysing the tumor cells and/or tumor supporting cells with a detergent solution prior to contact with the DCs. In some instances, the detergent is selected from, but is not limited to, Triton X-100, Triton X-114, NP-40, Brij-35, Brij-58, Tween 20, Tween 80, octyl glucoside, octyl thioglucoside, SDS, CHAPS, and CHAPSO. In some instances, the detergent solution is purified of peroxides, and other impurities. In some instances, the detergent is about 0.1% to about 10% v/v of the detergent solution. In some instances, the detergent is about 0.1% to about 5% v/v of the detergent solution. In some instances, the detergent is about 0.5% to about 5% v/v of the detergent solution. In some instances, the detergent is about 1% to about 10% v/v of the detergent solution. In some instances, the detergent is about 1% to about 5% v/v of the detergent solution. In some instances, the methods comprise lysing cells without shaking, vortexing, freezing, thawing, shear pressure, sonicating and/or heating the cells.

In some instances, methods for cell lysis described herein further comprise stopping or neutralizing the lysing. For example, cells may be washed with a buffered saline solution (phospho-buffered saline solution or Hank's balanced salt solution) to neutralize the lysing.

Combination Therapy

Provided herein are combination therapies comprising therapeutic agents disclosed herein with other types of therapies in order to achieve an optimal result. For example, in some instances, combination approaches to cancer immunotherapy may be more successful than single-axis attacks which tumors can mutate to avoid. In some embodiments, the therapy is a cancer therapy. Cancer therapies include, but are not limited to, chemotherapy, radiation, small molecule inhibitors, and monoclonal antibodies.

Provided herein are compositions and methods wherein dendritic cell vaccination is combined with an adjuvant effect of a virus to overcome tumor immune evasion mechanisms and deplete tumor cells. A schematic representation of the combination therapies disclosed herein is depicted in FIG. 1. Methods described here may be used to treat a subject 101 for cancer by obtaining 101 dendritic cells 102 and tumor cells 104 from the subject, exposing the dendritic cells to the tumor cells or tumor cell lysate 105, also referred to as "pulsing" the dendritic cells, to primed (or "activated") the dendritic cells, delivering 107 the resulting primed and tumor-targeting dendritic cells to the subject after the subject has had his/her immune system stimulated with the virus 108 (see, e.g., FIG. 1). Optionally, a tumor antigen that is not from the subject can be used for pulsing the dendritic cells.

Tumor immune evasion mechanisms are responsible for the lack of efficacy seen with most immunotherapy platforms. Compositions and methods described herein provide for a multi-pronged approach, combining physiological (hyperthermic reduction of tumor perfusion), immunological (activation of effector cells of the adaptive and innate immune system), and apoptosis-inducing pathways (sTRAIL) to destroy tumor cells. Using a virus, like Dengue virus (DV), as an adjuvant to activate many pathways working in synergy may support the eradication of mutated tumor cells, improving the clinical efficacy of the cancer immunotherapy. Methods described herein provide cancer immunotherapies based on multiple mechanisms of action in concert and result in a decline in the ability of the tumor cells to employ resistance methods compared to delivery of any single method along.

Provided herein are methods for treating a subject having a disease or condition, comprising: obtaining dendritic cells (DCs); incubating the DCs with at least one tumor cell antigen; administering a virus to the subject; and administering the DCs to the subject. In some instances, the dendritic cells are autologous dendritic cells. In some instances, the dendritic cells are allogeneic dendritic cells. In some instances, incubating the DCs with at least one tumor antigen comprises incubating the DCs with a tumor cell. In some instances, incubating the DCs with at least one tumor antigen comprises incubating the DCs with a tumor cell lysate. In some instances, incubating the DCs with at least one tumor antigen comprises incubating the DC with a peptide expressed by a tumor cell. In some embodiments, the condition or disease is cancer. In some embodiments, the virus is an Arbovirus. In some embodiments, the virus is a Dengue virus.

Disclosed herein are methods for treating cancer in a subject in need thereof, comprising: obtaining dendritic cells (DCs); incubating the DCs with at least one tumor cell antigen; administering a Dengue Virus Type 2 serotype strain to the subject; and administering the DCs to the subject. In some instances, the Dengue Virus Type 2 serotype strain is DENV-2 #1710. In some instances, the dendritic cells are autologous dendritic cells. In some instances, the dendritic cells are allogeneic dendritic cells. In some instances, incubating the DCs with at least one tumor antigen comprises incubating the DCs with a tumor cell. In some instances, incubating the DCs with at least one tumor antigen comprises incubating the DCs with a tumor cell lysate.

Administering the virus may increase cancer cell death or cancer cell lysis beyond that induced by DCs alone. Cancer cell death may be increased by at least about 10% to 25%, at least about 10% to about 50%, at least about 20% to about 100%, at least about at least about 20% to about 200%. Administering the virus may reduce the size of tumor lesions beyond that reduced by DCs alone. Tumor lesion size may decrease by at least about 10% to about 50%, at least about 10% to about 30%, at least about 15% to about 80%. Administering the virus may reduce the number of myeloid-derived suppressor cells (MDSC) in the tumor microenvironment beyond that decreased by DCs alone. Administering the virus may reduce the number of myeloid-derived suppressor cells (MDSC) in the tumor microenvironment by at least about 10% to about 65%, at least about 10% to about 85%, at least about 10% to about 100%, or at least about 10% to about 200%.

Dengue Viruses

Provided herein are methods for combination therapy comprising administering a Dengue virus (DV) and activated DCs disclosed herein to target tumor cells, wherein the DV is administered to a subject. As used herein, the term "Dengue virus" includes any serotype of Dengue virus serotypes 1, 2, 3, 4, or 5. The term Dengue virus may also encompass genetically modified DV, in vitro mutated DV, and combinations of DV or proteins/peptides thereof. The DV may be alive, dead, recombinant or a protein/peptide thereof.

In primary infections, the death rate from DV is very low (1 in 61,000 per Manson’s Tropical Diseases). The virus infects, but does not kill APC of the monocyte-macrophage and Dendritic Cell lineage. These infected APC then begin a cytokine cascade of the pro-inflammatory (TNF-alpha and IL-1 beta), and $T_H1$ (IL-2, IL-7, IL-12, IL-15, and IL-21) types. These cytokines may result in strong activation of both the adaptive (CTL) and innate (NK) immune systems. After a 3-5 day incubation period, the fever rises to 39.5-40.5° C., and remains elevated for 4-5 days. The subject experiences intense headache, joint pain, malaise, and sensitivity to light. A rash covering the chest, back, and sometimes legs and arms, may develop by day 3 of fever. Clinically, dengue infections result in lowered platelet counts leading to hemorrhage, which ranges from minor to life-threatening in case of shock syndrome. With proper supportive care based on judicious fluid management, recovery is complete in 99% of cases.

Dengue viruses are Arboviruses, and are transmitted exclusively by mosquitoes of the *Aedes aegypti* and *albopictus* species. The virus has a complex life cycle involving an unidentified forest-dwelling mammalian reservoir (possibly primates), and human hosts. The female mosquito takes a blood meal from an infected person, the virus replicates to a high infectious titer (10^5/ml), in gut epithelial cells, then is transmitted to another person when the mosquito withdraws its stylet using back pressure after another blood meal. Dengue epidemics infect 50 million persons annually, with several thousand deaths, usually children with inadequate treatment of secondary infection-related shock.

The Dengue virus genome encodes structural proteins, capsid protein C, membrane protein M, envelope protein E, and nonstructural proteins, NS1, NS2a, NS2b, NS3, NS4a, NS4b and NS5. In some instances, the Dengue virus is a live strain of the Dengue virus. In some instances, the Dengue virus is an attenuated strain of the Dengue virus. In some instances, the Dengue virus is a weakened strain of the Dengue virus. In some instances, the Dengue virus is selected the following serotypes of dengue virus: DENV-1, DENV-2, DENV-3, DENV-4, and DENV-5, and combinations thereof.

Dengue Viruses are positive-strand RNA viruses of the Togavirus Family, sub-family Flaviviridae, (Group B). The virus has an icoashederal geometry and is approximately 40-45 nanometers in diameter. The 11,000 base genome codes for a nucleocapsid (NC), protein, a prM membrane fusion protein, an envelope glycoprotein (E), and 5 non-structural proteins NS1-NS5. The NC protein forms the viral core, with the envelope spikes attached via the prM complex. The E glycoprotein is the main target of neutralizing antibodies, and the NS-3 and NS-4 proteins make up the main targets for CD4+ and CD8+CTL.

The dengue viruses make up five distinct serotypes, DENV-1 through DENV-5. The serotypes 2 and 4 are cross-neutralizing for IgG, and types 1 and 3 are also cross-neutralizing. Immunity is not complete, however, and dengue is unique among viral infections in that a subsequent infection by a non-cross-neutralizing serotype carries an increased risk of mortality due to shock syndrome from immune hyper-activation.

Provided herein are compositions and method using such compositions, wherein the composition comprises Dengue virus serotype 1, 2, 3, 4, or 5. In some instances, the DV is serotype 2. In some instances the DV serotype 2 is DENV-2 strain #1710. DENV-2 strain #1710 may be advantageous over other DV strains because it is milder at infecting subjects, and are therefore safer. Other more virulent strains may have a stronger anti-tumor effect, but they may not be suitable due to safety concerns. A more virulent strain, by way of non-limiting example, is DENV-2 strain #1584. The DENV-2 strain #1710 is from a sample taken from Puerto Rico in 1985 and characterized as type A from a restriction site specific RT-PCR analysis using 4 primers (see Table 1) specific to the envelope gene region. See Harris et al., Virology 253, 86-95 (1999). Restriction site specific RT-PCR with these primers produces amplification products of 582 base pairs, 754 base pairs, and possibly 676 base pairs. The DENV-2 strain #1710 is recorded in a CDC database as entry number 555. See Harris (1999). The DENV-2 strain #1710 was isolated during a Puerto Rican epidemic. This outbreak had 9,540 suspected cases of DV, with one suspected, but no confirmed deaths due to the virus, which indicates the toxicity of DEN-2 strain #1710 is very low and therefore suitable for the methods disclosed herein.

TABLE 1

Sequence and Position of Primers to Amplify DENV-2 #1710 virus

| Primer | Sequence | Genome Position | Strand |
|---|---|---|---|
| RSS1 | 5'-GGATCCCAAGAAGGGGCCAT-3' (SEQ ID NO: 3) | 1696-1715 | + |
| RSS2 | 5'-GGCAGCTCCATAGATTGCT-3 (SEQ ID NO: 4) | 2277-2259 | - |
| RSS3 | 5'-GGTGTTGCTGCAGATGGAA-3' (SEQ ID NO: 5) | 1524-1542 | + |
| RSS4 | 5'-GTGTCACAGACAGTGAGGT-3' (SEQ ID NO: 6) | 2371-2353 | - |

Certain characteristics of DV and DV infection may make this virus particularly useful for the methods disclosed herein. For example, a unique feature of DV is that primary infections result in activation of a $T_H1$-type response of CD4+ and CD8+ helper-inducer and cytotoxic-effector CTL. By infecting, but not killing the antigen presenting cell (APC), (e.g. dendritic cell), DV up-regulates CD80 and CD83 expression on the APC, resulting in a pro-inflammatory $T_H1$ cytokine profile. Primary DV infections induce a $T_H1$ type response with activated $CD4^+$ and $CD8^+$ effector T cells as well as lymphokine-activated killer cells. This may increase the likelihood of a complete response to a cancer immunotherapy, such as therapies utilizing the primed dendritic cells disclosed herein.

In some cases, Dengue viruses can provide a counter attack to a tumor immune evasion mechanism. The tumor immune evasion mechanism, by way of non-limiting example, may be low levels of MHC on the tumor cell to prevent CTL recognition, and the counter attack may be high Interferon-γ raising MHC levels by up-regulating MHC gene expression. The tumor immune evasion mechanism, also by way of non-limiting example, may be one or more point mutations in a tumor peptide to prevent TCR binding, and the counter attack may be stimulating lymphokine-activated killer cells or cytokine-induced killer cells to target "escaped" tumor cells expressing aberrant peptides or MHC. In some embodiments, the tumor immune evasion mechanism is tumor vessels lacking factors for CTL attachment and trafficking, and the counter attack is high TNF-α restores gaps by altering PECAM-1, restores ICAM-1/VCAM-1 expression and P and E-selectins. In some embodiments, the tumor immune evasion mechanism is FasL killing of $Fas^+$ CTL by triggering apoptosis, and the counter attack is high IL-6 and/or IL-151 protects $Fas^+$ CTL by up-regulating FLIP ligand. In some embodiments, the tumor immune evasion mechanism is HLA-G protects from NK Cells, and the counter attack may be high IL-2, IL-7, IL-12, and/or IL-15 raise activation of NK. The tumor immune evasion mechanism may be stromal barriers inhibit CTL and the counter attack may be high IFN-γ activates macrophages to $M_1$. The tumor immune evasion mechanism may be Myeloid-Derived Suppressor Cells, (MDSC) and the counter attack may be iNKT Cells decrease MDSC. The tumor immune evasion mechanism may be CTL inactivated by TGF-β and the counter attack may be $T_H1$ cytokines reactivate tolerant CTL. The tumor immune evasion mechanism may be Tumor PI-9 blocks CTL killing and the counter attack may be high CD8 & ICAM-1 expression restores low-avidity CTL recognition and lysis by stabilizing weak interactions between TCR and MHC+self-peptide. The tumor immune evasion mechanism may be T-regulatory cells block CTL and the counter attack may be high $CD4^{Helper}$ cells overcome $CD4^{Reg}$ cells.

In some embodiments, the methods comprise activating or enhancing the subject's immune response by administering Dengue virus to the subject. Activating or enhancing may comprise inducing or increasing expression of cytokines and inflammatory mediators. Expression of genes in cells of the subject that may be increased by DV infection, include, but are not limited to, IL-1 beta, IL-2, IL-7, IL-12, IL-15, IFN-alpha, IFN-gamma, TNF-alpha, TNF-beta, GM-CSF, CD8 antigen, ICOSLG, CCL3, CCL5, TRAIL, IP10, GNLY, GZMA, HLA-DRA, HLA-DP alpha1, HLA-DP beta 1, and ZAP70.

In some instances, the methods disclosed herein comprise administering DV to the subject, wherein the administering results in the release of TNF-α by the immune system. TNFα is an inflammatory cytokine with pleiotropic effects, including direct killing of tumor cells via TRAIL (TNF-Apoptosis-Inducing-Ligand). Increased levels of proteins corresponding to these genes may be observed in tissues and circulating fluids of the subject as well. Levels may be increased at least 2-fold. Levels may be increased between 2-fold and 1000-fold. Levels may be increased between 2-fold and 100-fold. Levels may be increased between 2-fold and 10-fold.

In some instances, administering DV induces high levels of soluble TRAIL (sTRAIL) from a variety of cells including γδCTL, activated M1 macrophages and plasmacytoid DC (pDC). In some instances, DV activates IFNβ, a multi-functional cytokine with a 10-fold higher affinity for the same receptor as IFNα. IFNβ has similar antiviral properties in suppressing transcription of viral RNA, but is much more potent than IFNα in inducing apoptosis in tumor cells. Nitric oxide and IFNβ could act in a synergistic fashion during dengue infection. These molecules may work in tandem to overcome resistance to apoptosis mediated by the high levels of sTRAIL induced by $M_1$ macrophages, pDC, and δγ CTL.

Activating or enhancing the immune system of the subject may comprise inducing or increasing cell types present in the subject. These cell types include, but are not limited to, CD8+CD44+62L-cells, CD4+CD44+$CD62L^{lo}$ cells, HLA-DR+CD8+ cells, Tia-1 CD8+ cells, VLA-4 CD8+ cells, ICAM-1 CD8+ cells, and LFA-1 CD8+ cells.

Cancer

Provided herein are methods for cancer therapy comprising administration of therapeutic agents disclosed herein. Methods described herein also provide for clearing cancer cells. In some instances, administering DV to the subject induces an immune response. In some instances, the immune response is potent as compared to a common virus, such as a common cold virus. In some instances, the immune response results in tumor regression. The methods disclosed herein may comprise developing DCs capable of inducing an immune response that results in eliminating all tumor cells in a subject's body.

DNA microarray analyses have revealed that hundreds of genetically distinct tumor clones may exist in a single subject with advanced tumor. There is a pattern of negative correlation between $O_2$ supply and genetic mutation rates. The majority of agents such as cytotoxic drugs, antibodies, and small molecules, are nearly always blood-borne, exerting a Darwinian selective pressure to tumor clones that evade therapeutic mechanisms. Clones with the lowest perfusion rates have both low drug exposure and high capacity to evade immune system detection, making them resistant to conventional therapies. Provided herein are methods for cancer cell targeting, comprising inducing fever hyperthermia by administering DV to the subject with cancer, starving low-flow, resistant clones with mutated phenotypes, leaving more genetically stable clones for elimination by activated lymphocytes and other arms of the immune system. In some instances, the methods comprise combining fever with activation of CTL and lymphokine-activated killer cells (LAK) by administering pulsed DCs, lead to higher response rates than with conventional cancer therapies (e.g. antibody drug conjugates, kinase inhibitors, small molecules, etc.) or CTLs alone. The immune suppression seen in subjects with advanced cancer is a complex and dynamic process. It involves tolerance to the tumor antigens themselves, which are usually recognized as "self" by CTL. In some instances, methods described herein comprise breaking this tolerance and achieving high levels of $T_H1$ cytokines, which DV infection induces.

Cancers targeted herein may be a recurrent and/or a refractory cancer. In some instances, the cancer is an acute cancer or a chronic cancer. In some instances, the cancer is an accelerated refractory cancer. In some instances, the cancer is in remission. In some instances, the cancer is a stage I, stage II, stage III, or stage IV cancer. In some instances, the cancer is a juvenile cancer or adult cancer. Examples of cancers include, but are not limited to, sarcomas, carcinomas, lymphomas or leukemias. In some instances, the cancer is a solid tumor or a liposarcoma.

In some instances, the cancer is a sarcoma. The sarcomas may be a cancer of the bone, cartilage, fat, muscle, blood vessels, or other connective or supportive tissue. In some instances, sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma). The sarcoma may comprise a Ewing's sarcoma.

In some instances, the cancer is a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. In some instances, the cancer is bladder cancer.

In some instances, the cancer is a neuroendocrine cancer. In some instances, the cancer is a pancreatic cancer. In some embodiments, the cancer is thyroid cancer. In some instances, the cancer is an epithelial cancer, breast cancer, endometrial cancer, ovarian cancer, stromal ovarian cancer, or cervical cancer. In some embodiments, the cancer is prostate cancer. In some instances, the cancer is a skin cancer. In some instances, the cancer is a neo-angiogenic skin cancer. In some instances, the cancer is a melanoma. In some instances, the cancer is a kidney cancer, a lung cancer. Exemplary lung cancers include, without limitation, a small cell lung cancer or a non-small cell lung cancer. In some instances, the cancer is a colorectal cancer, e.g., a gastric cancer or a colon cancer. In some instance, the cancer is a brain cancer. In some instances, the cancer is a brain tumor. In some instances, the cancer is a glioblastoma or an astrocytoma.

In some instances, the cancer is breast cancer. In some embodiments, the breast cancer is a triple negative breast cancer (negative for estrogen receptor, progesterone receptor and Her2). In some embodiments, the breast cancer is estrogen receptor positive (ER+).

In some instances, the cancer is a lung cancer. In some instances, the lung cancer is a non-small cell lung carcinoma (NSCLC), small cell lung carcinoma, or mesotheliomia. Examples of NSCLC include squamous cell carcinoma, adenocarcinoma, and large cell carcinoma. In some instances, the mesothelioma is a cancerous tumor of the lining of the lung and chest cavity (pleura) or lining of the abdomen (peritoneum). In some instances, the mesothelioma is due to asbestos exposure.

In some instances, the cancer is a central nervous system (CNS) tumor. In some instances, the CNS tumor is classified as a glioma or nonglioma. In some instances, the glioma is malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendrogliomas. Nongliomas include meningiomas, pituitary adenomas, primary CNS lymphomas, and medulloblastomas. In some instances, the cancer is a meningioma.

In some instances, the cancer is a blood cancer. In some instances, the cancer is leukemia. In some instances, the cancer is a myeloid leukemia. In some instances, the cancer is a lymphoma. In some instances, the cancer is a non-Hodgkin's lymphoma. In some instances, the cancer is selected from myelogenous leukemia, lymphoblastic leukemia, myeloid leukemia, an acute myeloid leukemia, myelomonocytic leukemia, neutrophilic leukemia, myelodysplastic syndrome, B-cell lymphoma, burkitt lymphoma, large cell lymphoma, mixed cell lymphoma, follicular lymphoma, mantle cell lymphoma, hodgkin lymphoma, recurrent small lymphocytic lymphoma, hairy cell leukemia, multiple myeloma, basophilic leukemia, eosinophilic leukemia, megakaryoblastic leukemia, monoblastic leukemia, monocytic leukemia, erythroleukemia, erythroid leukemia and hepatocellular carcinoma. In some instance, the cancer is a hematological malignancy. In some instance, the hematological malignancy is a B cell malignancy. In some instance, the cancer is a chronic lymphocytic leukemia. In some instance, the cancer is an acute lymphoblastic leukemia. In some instance, the cancer is a CD19-positive Burkitt's lymphoma. In some instance, the leukemia is an acute lymphocytic leukemia, acute myelocytic leukemia, chronic lymphocytic leukemia, or chronic myelocytic leukemia. Additional types of leukemias include, but are not limited to, hairy cell leukemia, chronic myelomonocytic leukemia, and juvenile myelomonocytic leukemia.

In some instances, the lymphoma develops from a B lymphocyte or T lymphocyte. Two major types of lymphoma are Hodgkin's lymphoma, previously known as Hodgkin's disease, and non-Hodgkin's lymphoma. In some instance, the Non-Hodgkin lymphoma is indolent. In some instance, the Non-Hodgkin lymphoma is aggressive. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenstrom macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Methods of Administration

Provided herein are methods for treatment of a condition in a subject comprising administering cells disclosed herein. The methods may comprise administering DC. The methods may comprise administering DCs after pulsing the DCs, without storing or shipping the DCs. The methods may comprise administering the DCs after storing or shipping the DCs. The methods may comprise administering DCs at a time point selected from about 1 hour to about 24 hours after pulsing the DC. The methods may comprise administering the DCs at a time point selected from about 1 day to about 30 days after pulsing the DCs. The methods may comprise administering the DCs at a time point selected from about 1 week to about 12 weeks after pulsing the DCs.

Provided herein are methods for treatment of a condition in a subject comprising administering DCs to a subject in need thereof. In some instances, the DCs are provided in a solution. In some instances, the DCs are administered by a route selected from subcutaneous injection, intramuscular injection, intradermal injection, percutaneous administration, intravenous ("i.v.") administration, intranasal administration, intralymphatic injection, and oral administration. In some embodiments, iv administration is preferable, eliciting a more desirable response than other forms of administration (e.g. subcutaneous injection). In some instances, the subject is infused with the DC by an intralymphatic microcatheter.

Methods described herein may comprise suspending or mixing cells in a solution for intravenous (i.v.) administration (e.g., a 0.9% NaCL solution). The i.v. DCs may traffic to the lungs, where some will be trapped, but the majority may pass to secondary lymphatic organs such as liver and spleen white pulp T-cell zones to prime the CTL.

In some instances, the Dengue virus is initially administered at least 24 hours before administering the dendritic cells. In some instances, the Dengue virus is initially administered between about 12 hours and about 96 hours before administering the dendritic cells. In some instances, the Dengue virus is initially administered between about 24 hours and about 72 hours before administering the primed dendritic cells. In some instances, the Dengue virus is initially administered between 1 day and 4 days before administering the primed dendritic cells. In some instances, the Dengue virus is administered only once. In some instances, the Dengue virus is administered more than once. In some instances, the Dengue virus is administered only before receiving dendritic cells. In some instances, the Dengue virus is administered after receiving the primed dendritic cells. In some instances, the Dengue virus is administered before and after receiving the primed dendritic cells.

As seen in FIG. 2, the methods may comprise administering primed DCs on Day 0, followed by two injection of virus, such that the entire treatment is conducted in a week or less. In some instances, the subject will only receive the entire treatment once. In some embodiments, the entire treatment is repeated not more than once. In some embodiments, the entire treatment is repeated not more than twice. In some embodiments, the entire treatment is repeated not more than three times. In some embodiments, the entire treatment is repeated not more than ten times.

In some instances, the methods comprise administering the Dengue virus at a dose of about 0.5 ml of $10^6$ pfu/ml. In some instances, the dose is between about $10^3$ pfu/ml and about $10^8$ pfu/ml. In some instances, the dose is between about $10^3$ pfu/ml and about $10^6$ pfu/ml.

In some instances, successful infection or inoculation of the subject with the Dengue virus is confirmed by the development of hyperthermia or fever. In some instances, successful infection or inoculation of the subject with the Dengue virus is confirmed by the presence or increase of circulating cytokines in the blood/plasma of the subject. Cytokines may include, but are not limited to, interleukin-2 and interferon-gamma.

In some instances, methods described herein comprise administering primed dendritic cells to a subject in need thereof only once. In some instances, the primed dendritic cells are administered more than once. In some instances, the primed dendritic cells are administered a first time and a second time, wherein the first time and the second time are separated by about 1 day, about 2 days, about 3 days, about 4 days, about 5 days, or about 6 days, about 8 days, about 10 days, about 12 days, or about 18 days. In some instances, the first time and the second time are separated by about 1 week, about 2 weeks, about 3 weeks, or about a month. In some instances, the first time and the second time are separated by more than a month. In some instances, the first time and the second time are separated by less than 12 months. In some instances, the first time and the second time are separated by more than 12 months.

In some instances, methods described herein provide for administering primed dendritic cells to a subject when the subject is hyperthermic. In some instances, primed dendritic cells are administered after the subject has spike a fever. In some instances, primed dendritic cells are administered after the subject's temperature has risen to between about 37.5° C. and about 42° C. In some instances, the primed dendritic cells are administered after the subject's temperature has risen to between about 38° C. and about 42° C. In some instances, the primed dendritic cells are administered after the subject's temperature has risen to at least about 38.5° C. In some instances, the primed dendritic cells are administered after the subject's temperature has risen to 38.5° C. In some instances, the primed dendritic cells are administered to the subject after the subject's temperature reaches 38 degrees Celsius or higher. In some instances, the subject's temperature is measured by a tympanic or oral method.

Methods for producing primed DC described herein may comprise activating T cells in vitro with the DCs produced by the methods disclosed herein. In some instances, the subject is incapable of mounting an effective immune response. For example, the subject may be immunocompromised. The subject may have received a therapy that renders them immunocompromised. The subject may have a disease that renders them immunocompromised. In this case, the methods may comprise contacting T cells from an HLA-matched subject with the DCs. Contacting the T cells with the DCs in vitro may induce a CTL response. Contacting the T cells with the DCs in vitro may also induce proliferation of the T cells.

EXAMPLES

Example 1. Generation and Pulsing of Murine Dendritic Cells (DC)

A method as described by Lutz M., et. al. (J. Immunol. Methods 223:77-92, 1999), was employed to generate mature DCs form mouse bone marrow. Bone marrow suspensions were incubated in petri dishes in medium supplemented with recombinant murine GM-CSF for 10 days. Non-adherent cells were collected, centrifuged and resuspended in medium containing GM-CSF and lipopolysaccharide. Two days later, the DCs were harvested and their viability was determined by trypan-blue exclusion. Purity of the DCs was determined by flow cytometry analysis. DCs were pulsed with the synthetic peptides at 10 μg/ml for 18 hours. After 18 hours of incubation, DCs were harvested, washed twice in HBSS, and resuspended in HESS for additional studies (see Example 2 and 3).

Figure 3:
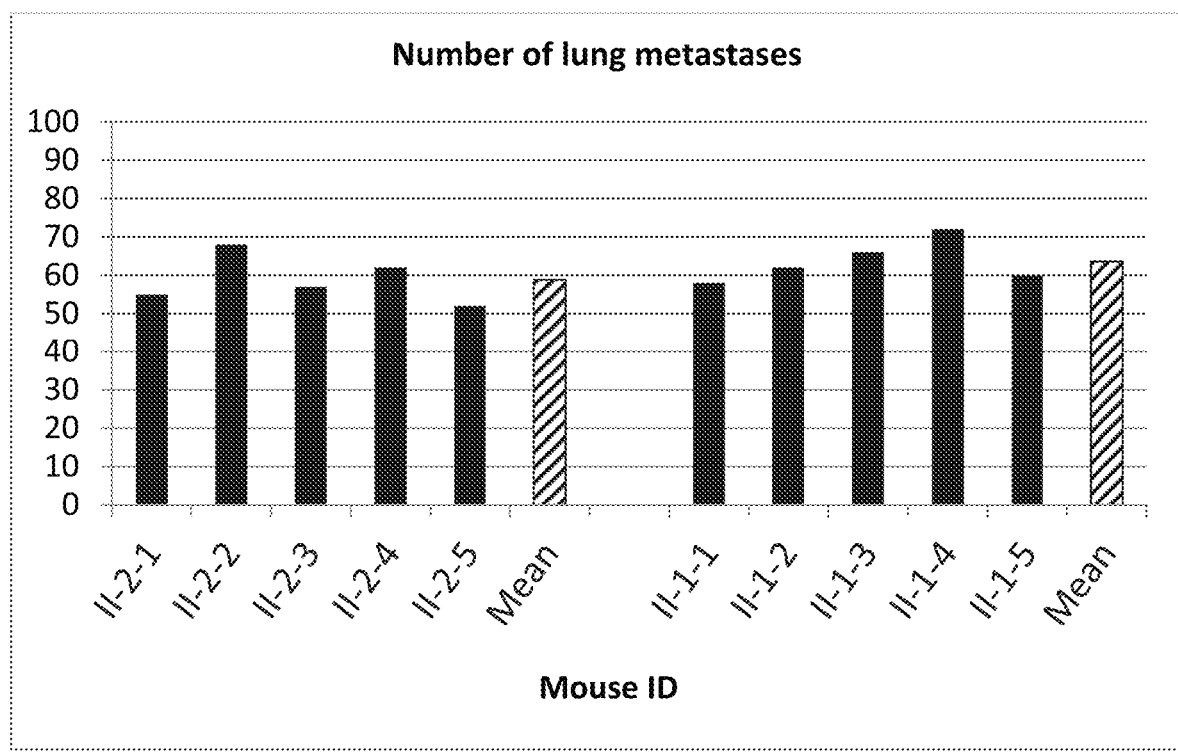

Example 2. Dengue Virus and Dendritic Cells for the Treatment of Melanoma in a First Mouse Model A mouse model assay was performed to observe results from combination targeting of cancer cells using a Dengue virus (DV) strain and tumor antigen primed dendritic cells (DCs). DV C57BL/6 mice were inoculated with 0.05 ml of Dengue virus (DEN-2 strain #1710) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 (rIL-2) and 500 1U (rIFN-gamma) on days 5, 10, 15, and 20 following administration of Dengue virus (DEN-2 strain #1710, CDC database entry number 555, provided by Dr. Duane Gubler). Seven days after the Dengue virus administration, C57BL/6 mice were immunized with mouse DCs incubated with the 2 peptides separately and injected intravenously. Peptides were synthesized. The H-2b-restricted peptide from Ovalbumin (OVA-8), SIINFEKL (SEQ ID NO: 7), was used as a control. B16 melanoma-associated H-2b-restricted peptides derived from the antigens gp100/pme117 (EGSRNQDWL (SEQ ID NO: 1)) and from TRP-1/75 (TAYRYHLL (SEQ ID NO: 2)) were used to pulse murine DCs (see Example 1 for details). Two additional immunizations with DCs were given at 14-day intervals. Three days after the last DC infusion, mice were challenged with $5\times10^4$ viable B16 melanoma cells intravenously in the lateral tail vein and then followed for survival, which was recorded as the percentage of surviving animals over time (in days) after tumor injection. Data was recorded from five or more mice/group (see Table 2 and FIG. 3).

TABLE 2

| Condition | Group | MOUSE ID | NO. OF LUNG METASTASES | Mean |
|---|---|---|---|---|
| $DV10^6$ pfu/ml + $2 \times 10^6$ DCs pulsed with gp100/TRP2 | 2 | II-2-1 | 55 | |
| $DV10^6$ pfu/ml + $2 \times 10^6$ DCs pulsed with gp100/TRP2 | 2 | II-2-2 | 68 | |
| $DV10^6$ pfu/ml + $2 \times 10^6$ DCs pulsed with gp100/TRP2 | 2 | II-2-3 | 57 | |
| $DV10^6$ pfu/ml + $2 \times 10^6$ DCs pulsed with gp100/TRP2 | 2 | II-2-4 | 62 | |
| $DV10^6$ pfu/ml + $2 \times 10^6$ DCs pulsed with gp100/TRP2 | 2 | II-2-5 | 52 | 58.8 |
| No DV + $2 \times 10^6$ DCs pulsed with gp100/TRP2 | 1 | II-1-1 | 58 | |
| No DV + $2 \times 10^6$ D DCs C pulsed with gp100/TRP2 | 1 | II-1-2 | 62 | |
| No DV + $2 \times 10^6$ DCs pulsed with gp100/TRP2 | 1 | II-1-3 | 66 | |
| No DV + $2 \times 10^6$ DCs pulsed with gp100/TRP2 | 1 | II-1-4 | 72 | |
| No DV + $2 \times 10^6$ DCs pulsed with gp100/TRP2 | 1 | II-1-5 | 60 | 63.6 |

The number of lung metastases observed in mice administered in Group 2 (Dengue Virus serotype 2 strain #1710 and tumor peptide primed DCs) was 7.5% lower than control mice in Group 1, administered the tumor peptide primed DCs without the Dengue virus.

Example 3. Dengue Virus and Dendritic Cells for the Treatment of Melanoma in a Second Mouse Model A mouse model assay was performed to observe results from combination targeting of cancer cells using a Dengue virus (DV) strain and tumor antigen primed dendritic cells (DCs). Mice were administered cytokines to parallel the response to DV observed in humans.

Tumors were established in mice using the $H-^2b$-restricted B16 murine melanoma cells line (ATCC #CRL-6322). Peptides (B16 melanoma associated $H-^2b$-restricted peptides derived from antigens gp100/pme117 and from TRP-1/gp75 used for pulsing the dendritic cells were synthesized. Dendritic cells were generated from mouse bone marrow according to methods as described in Lutz et al. (J. Immunol. Methods 223:77-92, 1999).

On day 0, mice received $5\times10^4$ viable B16 melanoma cells intravenously in the lateral tail vein to establish pulmonary metastases. On day 7, the mice were inoculated with 0.05 ml of Dengue virus (DEN-2 strain #1710, CDC database entry number 555) at $1\times10^6$ or $1\times10^7$ pfu/ml by injection in the base of tail. Recombinant murine IL-2 (Genzyme) and IFN-gamma (Sigma Pharmaceuticals) were administered by intravenous infusion at 2,000 1U (rIL-2) and 500 1U (rIFN-gamma) at 5-day intervals following administration of Dengue virus (DEN-2 strain #1710). On days 21, 35 and 49, the mouse DCs were incubated with the 2 peptides separately and injected intravenously in 2 sequential administrations on the same day to match the route and schedule of administration in subjects (see Example 2 for additional details). Control groups of mice received no Dengue virus or dendritic cells pulsed with H-$^2$b-restricted peptide from ovalbumin (OVA-8), SIINFKEL. Treatment and control groups are shown in Table 3.

TABLE 3

| Dengue Virus | # of dendritic cells and type of peptide |
|---|---|
| Group A | |
| 10$^6$ pfu/ml | 10$^6$ DCs pulsed with gp100/pme117 (EGSRNQDWL)(SEQ ID NO: 1) |
|  | 10$^6$ DCs pulsed with TRP-1/gp75 (TAYRYHLL)(SEQ ID NO: 2) |
| Total | 2 × 10$^6$ DCs pulsed with peptide/mouse |
| Group B | |
| 10$^6$ pfu/ml | 10$^7$ DCs pulsed with gp100/pme117 (EGSRNQDWL)(SEQ ID NO: 1) |
|  | 10$^7$ DCs pulsed with TRP-1/gp75 (TAYRYHLL)(SEQ ID NO: 2) |
| Total | 2 × 10$^7$ DCs pulsed with peptide/mouse |
| Group C - Control | |
| None | 10$^6$ DCs pulsed with gp100/pme117 (EGSRNQDWL)(SEQ ID NO: 1) |
|  | 10$^6$ DCs pulsed with TRP-1/gp75 (TAYRYHLL)(SEQ ID NO: 2) |
| Total | 2 × 10$^6$ DCs pulsed with peptide/mouse |
| Group D - Control | |
| 10$^6$ pfu/ml | 10$^6$ DCs pulsed with OVA (SIINFKEL)(SEQ ID NO: 7) |
|  | 10$^6$ DCs pulsed with OVA (SIINFKEL)(SEQ ID NO: 7) |
| Total | 2 × 10$^6$ DCs pulsed with peptide/mouse |

Figure 4:
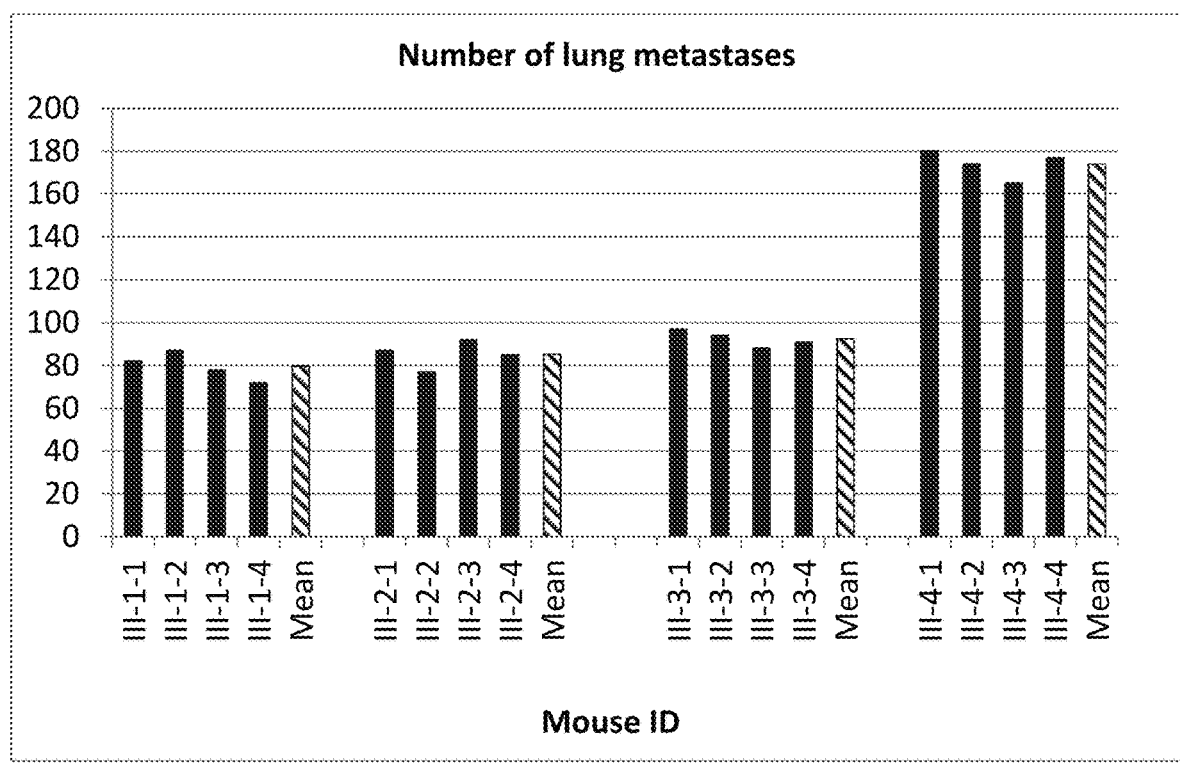
Figure 5:
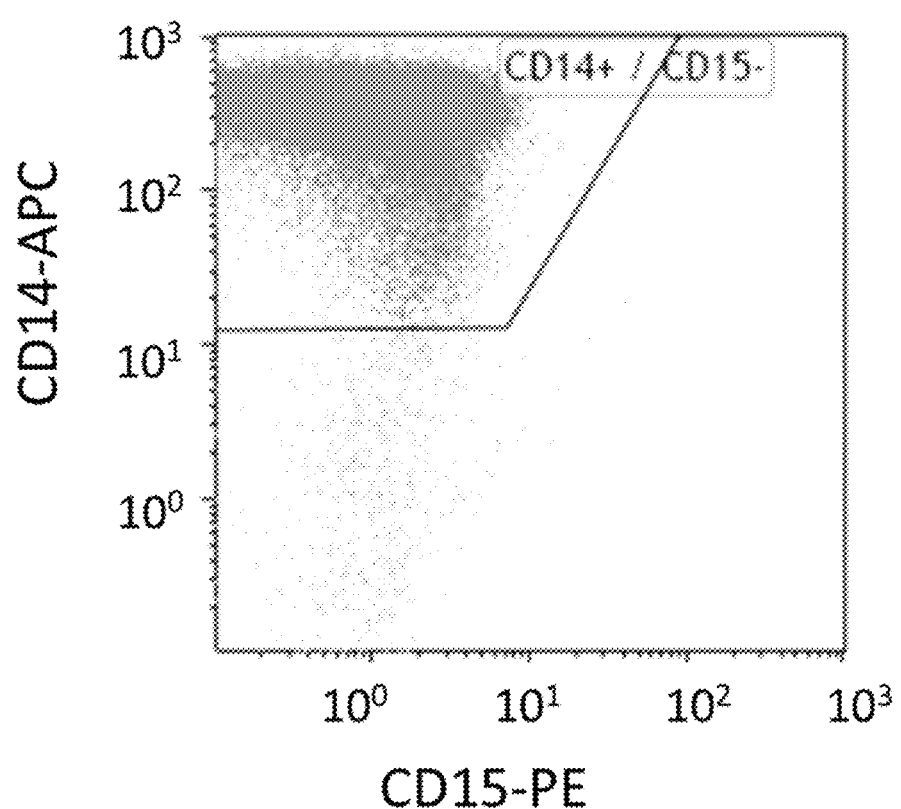

On day 90, animals were sacrificed and lung tumor colonies were counted. Pulmonary metastases were enumerated in a blinded, coded fashion after insufflation and fixation of the lungs with Fekette's solution. Data were reported as the mean number of metastases; four mice/group (see Table 4 and FIG. 4). Histopathology of the following major organ systems were performed: brain, heart, lungs, liver, kidneys, spleen and gonads (data not shown).

TABLE 4

| Condition | Group | MOUSE ID | NO. OF LUNG METASTASES | Mean |
|---|---|---|---|---|
| DV10$^6$ pfu/ml + 2 × 10$^6$ DC pulsed with gp100/TRP2 | A | III-1-1 | 82 | |
| DV10$^6$ pfu/ml + 2 × 10$^6$ DC pulsed with gp100/TRP2 | A | III-1-2 | 87 | |
| DV10$^6$ pfu/ml + 2 × 10$^6$ DC pulsed with gp100/TRP2 | A | III-1-3 | 78 | |
| DV10$^6$ pfu/ml + 2 × 10$^6$ DC pulsed with gp100/TRP2 | A | III-1-4 | 72 | |
| | | | | 79.75 |
| DV10$^7$ pfu/ml + 2 × 10$^6$ DC pulsed with gp100/TRP2 | B | III-2-1 | 87 | |
| DV10$^6$ pfu/ml + 2 × 10$^6$ DC pulsed with gp100/TRP2 | B | III-2-2 | 77 | |
| DV10$^6$ pfu/ml + 2 × 10$^6$ DC pulsed with gp100/TRP2 | B | III-2-3 | 92 | |
| DV10$^6$ pfu/ml + 2 × 10$^6$ DC pulsed with gp100/TRP2 | B | III-2-4 | 85 | |
| | | | | 85.25 |
| No dengue virus + 2 × 10$^6$ DC pulsed with gp100/TRP2 | C | III-3-1 | 97 | |
| No dengue virus + 2 × 10$^6$ DC pulsed with gp100/TRP2 | C | III-3-2 | 94 | |
| No dengue virus + 2 × 10$^6$ DC pulsed with gp100/TRP2 | C | III-3-3 | 88 | |

TABLE 4-continued

| Condition | Group | MOUSE ID | NO. OF LUNG METASTASES | Mean |
|---|---|---|---|---|
| No dengue virus + 2 × 10$^6$ DC pulsed with gp100/TRP2 | C | III-3-4 | 91 | |
| | | | | 92.5 |
| DV10$^6$ pfu/ml + 2 × 10$^6$ DC pulsed with OV | D | III-4-1 | 180 | |
| DV10$^6$ pfu/ml + 2 × 10$^6$ DC pulsed with OV | D | III-4-2 | 174 | |
| DV10$^6$ pfu/ml + 2 × 10$^6$ DC pulsed with OV | D | III-4-3 | 165 | |
| DV10$^6$ pfu/ml + 2 × 10$^6$ DC pulsed with OV | D | III-4-4 | 177 | |
| | | | | 174 |

The number of lung metastases observed in mice in Group C (administered tumor antigen primed DCs and no virus) was 47% less than control Group D (administered DENV-2 #1710 and DCs exposed to a control peptide). The number of lung metastases observed in mice in Group A (administered DENV-2 #1710 and tumor antigen primed DCs) was 54% less than control Group D (administered DENV-2 #1710 and DCs exposed to a control peptide). The number of lung metastases observed in mice in Group B (administered DENV-2 #1710 and tumor antigen primed DCs) was 51% less than control Group D (administered DENV-2 #1710 and DCs exposed to a control peptide). The average reduction in Group A and B compared to Group D was 52.8%.

Example 4. Manufacture and Screening of Less-Pathogenic Dengue Virus

A Master Cell Bank with validated and certified cell lines from Vero (African Green Monkey Kidney Cells) was generated and tested for absence of any contaminants and adventitious organisms. Vero lines are used by the World Health Organizations to produce a variety of viral vaccines. Dengue virus was passaged in a validated Vero Line derived from the Master Cell Bank and established as a Working Cell Bank according to guidelines established by the FDA Center for Biologics (CBER). Two Dengue Virus Type 2 strains (DNV-2 #1584 and DENV-2 #1710) from initial seed stocks were added to the Vero Cells of the WCB at a MOI of $10^{-5}$.

The first 4-ml overlay medium—containing 1% SeaKem LE agarose (FMC BioProducts, Rockland, Me.) in nutrient medium (0.165% lactalbumin hydrolysate [Difco Laboratories, Detroit, Mich.]), 0.033% yeast extract [Difco], Earle's balanced salt solution, 25 mg of gentamicin sulfate [Bio-Whittaker, Walkersville, Md.] and 1.0 mg of amphotericin B [Fungizone; E. R. Squibb & Sons, Princeton, N.J.], per liter and 2% FBS)—was added after adsorption of the 200-ml virus inoculum for 1.5 h at 37° C. Following incubation at 37° C. for 7 days, a second 2-ml overlay containing additional 80 mg of neutral red vital stain (GIBCO-BRL, Gaithersburg, Md.) per ml was added. Plaques were counted 8 to 11 days after infection.

A plaque assay on final virus cultures was performed. The titer of DNV-2 #1584 was about 5E+06 PFU/ml, and the titer of DENV-2 #1710 was 3.5E+06 pfu/mL as estimated from plaque assays. Dengue virus 2 (DNV-2; #1584) from ATCC showed a clear cytopathic effect in Vero cells 5 days post infection, whereas Vero cells appears to have a morphology change 11 days post infection of the blind passage #2 (#1710 virus). (Data not shown.) The assay shows that the DENV-2 #1710 virus is far less cytopathic than the DNV-2 #1584 strain Example 5. Cancer Killing Assay with Pulsed DC, with and without DV In a control arm, normal human tumor infiltrating lymphocytes (TILs) were directly applied to human melanoma FEMX cells. T-cell receptors were matched to FEMX melanoma cell line via HLA A2.1+. In a treatment arm human TILs were exposed to DV supernatants containing interferons and interleukins. Exposed TILs+DV supernatants were placed in culture with FEMX tumor cells. Both arms were left to kill cancer cells for 4 hours at a ratio of 5-to-1T-cell to tumor cell (100,000 cells to 20,000 cells). Surviving tumor cells were then counted as % of starting cells by flow cytometry. Results, shown in Table 5, demonstrate that DV induces 35% additional cancer cell killing beyond the pulsed DC anti-cancer response.

TABLE 5

DV enhancement of pulsed DC anti-cancer activity

| | % FL2-A− | % FL2-A+ (% Apoptotic Cells) |
|---|---|---|
| CTL | 86.1% | 13.9% |
| CTL + DV Sups | 81.2% | 18.8% |

Example 6. Human Dendritic Cell Isolation and Pulse with Melanoma Lysate Antigens The following example demonstrates generation of a highly pure CD11a+ mature DC population expressing high levels of human IL-12p70 from pure, isolated CD14+ monocytes, as well as priming of the DC with melanoma cell lysate, the entire process being completed in less than one week. Cells were cultured on hard plastic plates and not exposed to soft plastic bags.

CD14+ monocytes were isolated and analyzed for expression of CD14, CD15, CD45 and 7AAD. Post-prodigy run, 90.25% of input cells were CD14+(see FIG. 5). CD14+ cells were treated with GM-CSF and IL-4 24 hours post plating to generate immature dendritic cells.

RPMI-7951 melanoma cells from ATCC arrived on the day of the prodigy run and were re-suspended, counted and plated. Melanoma cells were than treated with a calcium hypochlorite solution. Alternatively, cells were treated with sodium chlorite solution. The melanoma cell lysate was added to the immature DC, and maturing agents IFN gamma (1000U/mL), R848 (5 μg/mL) and LPS (long/mL) were added.

Figure 6:
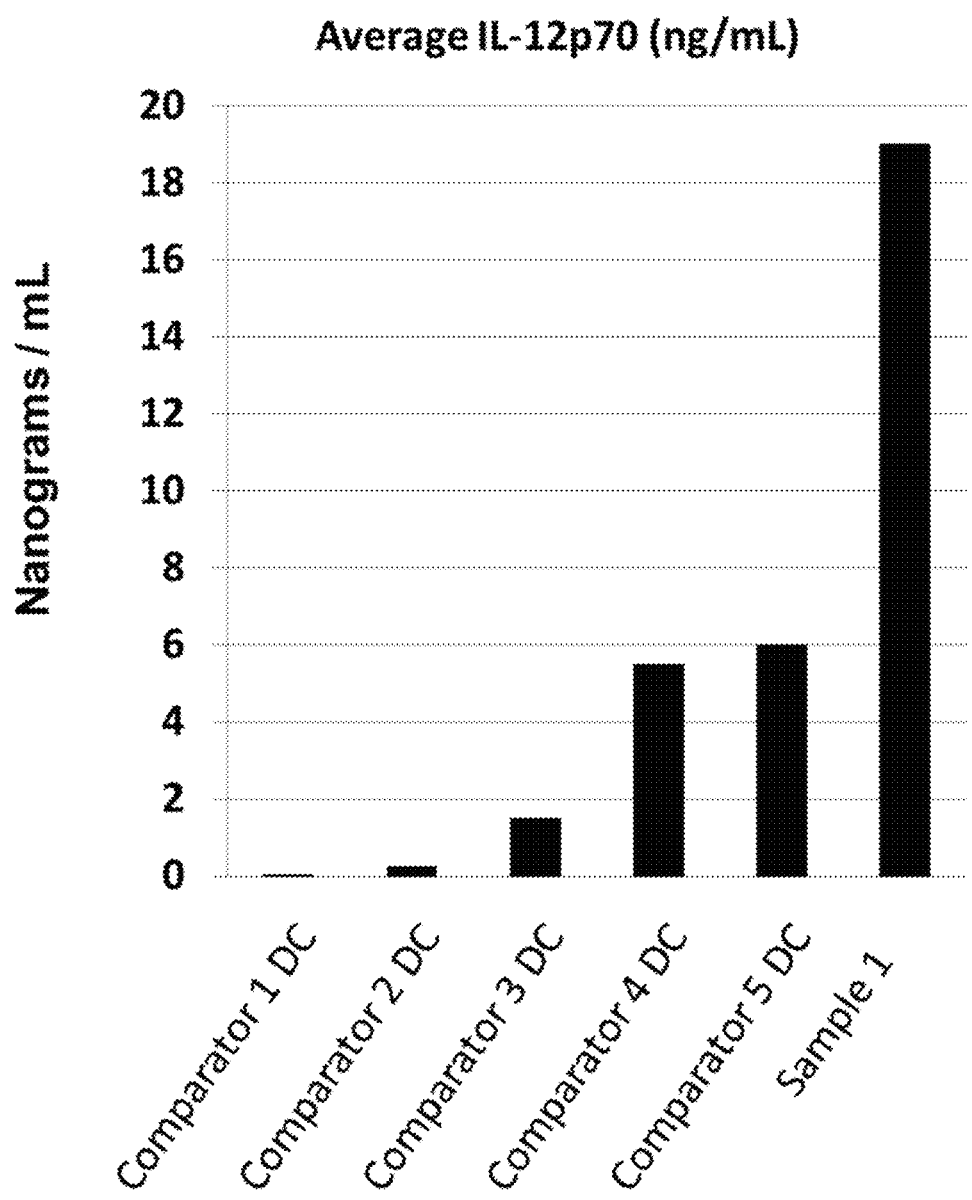

Supernatant from mature DCs were collected and examined for *mycoplasma* and endotoxin 22 hours after pulsing with melanoma cell lysate and 18 hours after addition of maturing agents. No pathogenic organisms were observed. An ELISA assay was performed to measure IL-12p70 levels, using supernatant from the DC culture medium. The concentration of IL-12p70 was 19+/−4 ng/mL in a first batch of cells, as opposed to the industry standard of 4-6 ng/mL. Various batches of cells produced by the same protocol showed concentrations of 15-23 ng/mL IL-12p70. A viability assay was conducted and average viability was recorded at 79.2% after cells were frozen, thawed and cultured (compared to a comparator which showed 70%). FIG. 6 shows DC IL-12p70 production (see Sample 1 of FIG. 6) relative to that of several comparators. These comparators methods include exposing cells to soft plastic bags, lysing cells with solutions other than a chlorite solution, and do not use the combination of LPS, IFN gamma and R848 to mature cells.

Cells were further frozen and then thawed at 4° C. to test cell counts and viability after freezing and thawing. These were measured at approximately 16 h, 18 h, 20 h and 22 h after beginning of thaw. See Table 6 for results. An extra harvest of non-pulsed DCs were tested in a cryopreservation study, and showed greater than 70% viability. Pre-cryopreservation viability ranged from 85-89%.

TABLE 6

Pulsed DC viability after freeze-thaw

| Time post start thaw | Viability | Total Live Cells in 30 ml |
|---|---|---|
| 16 h | 68.9% | $8.52 \times 10^6$ |
| 18 h | 67.9% | $8.25 \times 10^6$ |
| 20 h | 66.3% | $7.23 \times 10^6$ |
| 22 h | 70.3% | $11.46 \times 10^6$ |

Switch from these slow thaws (16 h to 22 h, shown in Table 6) to a rapid thaw (37° C. water bath for about 30 sec to about 5 minutes), resulted in viability from 71-79%.

Cells not pulsed were used as a cryopreservation study. Viability ranged from 71.4% to 79.2%.

Example 7. Inducing Cytokines in Human White Blood Cells with Dengue Virus

Human white blood cells (WBC), including monocytes, dendritic cells and T lymphocytes, were infected with either mock virus or Dengue virus at three different multiplicities of infection (MOD, MOI of 0.1, MOI of 0.5 and MOI of 2 at time=0. Levels (pg/mL) of various cytokines were measured at 48 h, 72 h and 96 h, post-infection. Treatments were performed in triplicate. Results are shown for each time point in Tables 7-9. (M=mock. 0.1, 0.5 and 2 are MOI). Triplicate average of changes between mock and Dengue virus at the assessed MOIs was calculated and shown as a percentage in Table 10.

TABLE 7

Cytokine levels produced by human WBC, 48 h post- Dengue virus infection

|  | M | M | M | 0.1 | 0.1 | 0.1 |
|---|---|---|---|---|---|---|
| IL-1b | 15 | 6 | 6 | 6 | 6 | 6 |
| IL-10 | 4 | 4 | 4 | 4 | 4 | 4 |
| IL-13 | 11 | 11 | 11 | 11 | 11 | 11 |
| IL-6 | 12 | 7 | 9 | 941 | 874 | 788 |
| IL-12 | 19 | 12 | 13 | 14 | 15 | 15 |
| Rantes | 12 | 11 | 11 | 14 | 16 | 18 |
| CCL-11 | 3 | 3 | 3 | 3 | 3 | 3 |
| IL-17 | 18 | 18 | 18 | 18 | 18 | 18 |
| MIP-1a | 123 | 110 | 109 | 183 | 166 | 219 |
| GM-CSF | 5 | 5 | 5 | 5 | 5 | 5 |
| MIP-1b | 83 | 78 | 82 | 123 | 111 | 118 |
| MCP-1 | 1.77e+03 | 1.48e+03 | 1.87e+03 | 12.6e+03 | 10.4e+03 | 9.95e+03 |
| IL-15 | 33 | 33 | 33 | 33 | 33 | 33 |
| IL-5 | 8 | 8 | 8 | 8 | 8 | 8 |
| IFN-g | 5 | 5 | 5 | 6 | 6 | 6 |
| IFN-a | 16 | 12 | 12 | 37 | 35 | 33 |
| IL-1Ra | 3.37e+03 | 2.84e+03 | 3.59e+03 | 4.99e+03 | 4.39e+03 | 4.30e+03 |
| TNF-a | 6 | 6 | 6 | 8 | 8 | 8 |
| IL-2 | 9 | 9 | 9 | 9 | 9 | 9 |
| IL-7 | 16 | 8 | 11 | 31 | 27 | 26 |
| IP-10 | 4 | 4 | 4 | 23 | 15 | 18 |
| IL-2R | 31 | 31 | 31 | 54 | 47 | 52 |
| MIG | 38 | 32 | 39 | 29 | 26 | 26 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
|  | 0.5 | 0.5 | 0.5 | 2 | 2 | 2 |
| IL-1b | 6 | 6 | 6 | 7 | 7 | 7 |
| IL-10 | 4 | 4 | 5 | 5 | 4 | 4 |
| IL-13 | 11 | 11 | 11 | 11 | 11 | 11 |
| IL-6 | 8.08e+03 | 8.64e+03 | 10.0e+03 | 11.2e+03 | 11.2e+03 | 11.2e+03 |
| IL-12 | 17 | 20 | 19 | 28 | 25 | 25 |

TABLE 7-continued

Cytokine levels produced by human WBC, 48 h post- Dengue virus infection

| | | | | | | |
|---|---|---|---|---|---|---|
| Rantes | 32 | 56 | 64 | 152 | 135 | 148 |
| CCL-11 | 3 | 3 | 3 | 3 | 3 | 3 |
| IL-17 | 18 | 18 | 18 | 18 | 18 | 18 |
| MIP-1a | 212 | 309 | 328 | 261 | 264 | 259 |
| GM-CSF | 5 | 6 | 7 | 22 | 20 | 21 |
| MIP-1b | 145 | 152 | 142 | 163 | 149 | 155 |
| MCP-1 | 21.8e+03 | 23.4e+03 | 24.2e+03 | 32.0e+03 | 32.0e+03 | 32.0e+03 |
| IL-15 | 33 | 33 | 33 | 68 | 63 | 60 |
| IL-5 | 16 | 18 | 18 | 21 | 21 | 20 |
| IFN-g | 8 | 8 | 8 | 10 | 9 | 10 |
| IFN-a | 47 | 50 | 47 | 67 | 68 | 71 |
| IL-1Ra | 4.55e+03 | 4.88e+03 | 5.14e+03 | 4.13e+03 | 3.42e+03 | 3.82e+03 |
| TNF-a | 16 | 13 | 11 | 21 | 21 | 19 |
| IL-2 | 9 | 9 | 9 | 9 | 9 | 9 |
| IL-7 | 51 | 49 | 47 | 53 | 55 | 54 |
| IP-10 | 39 | 46 | 39 | 218 | 128 | 147 |
| IL-2R | 57 | 69 | 69 | 79 | 76 | 79 |
| MIG | 26 | 31 | 28 | 23 | 22 | 27 |
| IL-4 | 27 | 27 | 27 | 30 | 29 | 30 |
| IL-8 | 17.8e+03 | 17.8e+03 | 17.8e+03 | 17.8e+03 | 17.8e+03 | 17.8e+03 |

TABLE 8

Cytokine levels produced by human WBC, 72 h post- Dengue virus infection

| | M | M | M | 0.1 | 0.1 | 0.1 |
|---|---|---|---|---|---|---|
| IL-1b | 6 | 6 | 6 | 6 | 6 | 6 |
| IL-10 | 4 | 4 | 4 | 4 | 4 | 4 |
| IL-13 | 11 | 11 | 11 | 11 | 11 | 11 |
| IL-6 | 7 | 7 | 7 | 637 | 690 | 737 |
| IL-12 | 12 | 11 | 11 | 12 | 12 | 14 |
| Rantes | 11 | 11 | 11 | 11 | 11 | 11 |
| CCL-11 | 3 | 3 | 3 | 3 | 3 | 3 |
| IL-17 | 18 | 18 | 18 | 18 | 18 | 18 |
| MIP-1a | 96 | 88 | 88 | 84 | 97 | 118 |
| GM-CSF | 5 | 5 | 5 | 5 | 5 | 5 |
| MIP-1b | 83 | 78 | 80 | 85 | 90 | 101 |
| MCP-1 | 5.51e+03 | 5.02e+03 | 4.87e+03 | 21.5e+03 | 22.4e+03 | 21.7e+03 |
| IL-15 | 33 | 33 | 33 | 33 | 33 | 33 |
| IL-5 | 8 | 8 | 8 | 8 | 8 | 8 |
| IFN-g | 5 | 5 | 5 | 6 | 6 | 6 |
| IFN-a | 26 | 23 | 24 | 43 | 46 | 46 |
| IL-1Ra | 6.30e+03 | 5.97e+03 | 6.02e+03 | 6.36e+03 | 6.89e+03 | 6.36e+03 |
| TNF-a | 6 | 6 | 6 | 6 | 6 | 6 |
| IL-2 | 9 | 9 | 9 | 9 | 9 | 9 |
| IL-7 | 8 | 8 | 8 | 23 | 25 | 21 |
| IP-10 | 4 | 4 | 4 | 18 | 14 | 17 |
| IL-2R | 31 | 28 | 20 | 42 | 44 | 42 |
| MIG | 40 | 35 | 35 | 32 | 28 | 27 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
| | 0.5 | 0.5 | 0.5 | 2 | 2 | 2 |
| IL-1b | 6 | 6 | 6 | 6 | 7 | 7 |
| IL-10 | 5 | 5 | 4 | 4 | 5 | 5 |
| IL-13 | 11 | 11 | 11 | 11 | 11 | 11 |
| IL-6 | 5518 | 8803 | 6841 | 11.2e+03 | 11.2e+03 | 11.2e+03 |
| IL-12 | 15 | 17 | 16 | 17 | 20 | 22 |

TABLE 8-continued

Cytokine levels produced by human WBC, 72 h post- Dengue virus infection

| | | | | | | |
|---|---|---|---|---|---|---|
| Rantes | 11 | 16 | 15 | 21 | 88 | 68 |
| CCL-11 | 3 | 3 | 3 | 3 | 3 | 3 |
| IL-17 | 18 | 18 | 18 | 18 | 18 | 18 |
| MIP-1a | 91 | 118 | 106 | 54 | 133 | 87 |
| GM-CSF | 5 | 5 | 5 | 8 | 15 | 15 |
| MIP-1b | 104 | 112 | 101 | 84 | 98 | 101 |
| MCP-1 | 32.0e+03 | 32.0e+03 | 32.0e+03 | 32.0e+03 | 32.0e+03 | 32.0e+03 |
| IL-15 | 33 | 33 | 33 | 33 | 38 | 67 |
| IL-5 | 14 | 15 | 14 | 17 | 19 | 20 |
| IFN-g | 8 | 8 | 7 | 6 | 8 | 8 |
| IFN-a | 62 | 56 | 52 | 61 | 66 | 67 |
| IL-1Ra | 6.90e+03 | 6.76e+03 | 6.01e+03 | 4.33e+03 | 3.89e+03 | 4.39e+03 |
| TNF-a | 6 | 6 | 6 | 6 | 6 | 6 |
| IL-2 | 9 | 9 | 9 | 9 | 9 | 9 |
| IL-7 | 42 | 40 | 40 | 45 | 50 | 48 |
| IP-10 | 42 | 38 | 38 | 104 | 143 | 169 |
| IL-2R | 42 | 47 | 47 | 44 | 56 | 60 |
| MIG | 27 | 25 | 22 | 24 | 19 | 25 |
| IL-4 | 27 | 25 | 24 | 26 | 27 | 29 |
| IL-8 | 17.8e+03 | 17.8e+03 | 17.8e+03 | 17.8e+03 | 17.8e+03 | 17.8e+03 |

TABLE 9

Cytokine levels produced by human WBC, 96 h post- Dengue virus infection

| | M | M | M | 0.1 | 0.1 | 0.1 |
|---|---|---|---|---|---|---|
| IL-1b | 6 | 6 | 6 | 6 | 6 | 6 |
| IL-10 | 4 | 4 | 4 | 5 | 4 | 4 |
| IL-13 | 11 | 11 | 11 | 11 | 11 | 11 |
| IL-6 | 9 | 9 | 9 | 834 | 734 | 771 |
| IL-12 | 14 | 13 | 13 | 16 | 14 | 14 |
| Rantes | 11 | 11 | 11 | 11 | 11 | 11 |
| CCL-11 | 3 | 3 | 3 | 3 | 3 | 3 |
| IL-17 | 18 | 18 | 18 | 18 | 18 | 18 |
| MIP-1a | 98 | 89 | 119 | 73 | 103 | 122 |
| GM-CSF | 5 | 5 | 5 | 5 | 5 | 5 |
| MIP-1b | 82 | 78 | 99 | 63 | 89 | 99 |
| MCP-1 | 8.19e+03 | 7.61e+03 | 7.10e+03 | 32.0e+03 | 25.3e+03 | 25.6e+03 |
| IL-15 | 33 | 33 | 33 | 33 | 33 | 33 |
| IL-5 | 8 | 8 | 8 | 8 | 8 | 8 |
| IFN-g | 6 | 6 | 7 | 8 | 7 | 6 |
| IFN-a | 27 | 29 | 27 | 52 | 47 | 44 |
| IL-1Ra | 10.9e+03 | 10.9e+03 | 10.2e+03 | 11.0e+03 | 9.57e+03 | 9.56e+03 |
| TNF-a | 6 | 6 | 6 | 6 | 6 | 6 |
| IL-2 | 9 | 9 | 9 | 9 | 9 | 9 |
| IL-7 | 8 | 8 | 8 | 21 | 18 | 14 |
| IP-10 | 4 | 4 | 4 | 29 | 11 | 11 |
| IL-2R | 25 | 23 | 28 | 39 | 36 | 42 |
| MIG | 39 | 40 | 39 | 39 | 24 | 26 |
| IL-4 | 23 | 23 | 23 | 23 | 23 | 23 |
| IL-8 | 17.8e+03 | 17.8e+03 | 17.8e+03 | 17.8e+03 | 17.8e+03 | 17.8e+03 |
| | 0.5 | 0.5 | 0.5 | 2 | 2 | 2 |
| IL-1b | 6 | 6 | 7 | 7 | 6 | 7 |
| IL-10 | 5 | 6 | 6 | 5 | 5 | 5 |
| IL-13 | 11 | 11 | 11 | 11 | 11 | 11 |
| IL-6 | 7026 | 7.47e+03 | 7.65e+03 | 11.2e+03 | 11.2e+03 | 11.2e+03 |
| IL-12 | 16 | 14 | 16 | 16 | 20 | 20 |

TABLE 9-continued

Cytokine levels produced by human WBC, 96 h post- Dengue virus infection

| | | | | | | |
|---|---|---|---|---|---|---|
| Rantes | 11 | 11 | 11 | 37 | 70 | 68 |
| CCL-11 | 3 | 3 | 3 | 3 | 3 | 3 |
| IL-17 | 18 | 18 | 18 | 18 | 18 | 18 |
| MIP-1a | 79 | 77 | 85 | 60 | 108 | 106 |
| GM-CSF | 5 | 5 | 5 | 12 | 14 | 15 |
| MIP-1b | 85 | 83 | 89 | 67 | 72 | 76 |
| MCP-1 | 32.0e+03 | 32.0e+03 | 32.0e+03 | 32.0e+03 | 32.0e+03 | 32.0e+03 |
| IL-15 | 33 | 33 | 33 | 49 | 43 | 52 |
| IL-5 | 15 | 16 | 16 | 20 | 19 | 18 |
| IFN-g | 7 | 7 | 7 | 7 | 7 | 7 |
| IFN-a | 56 | 58 | 65 | 64 | 64 | 67 |
| IL-1Ra | 7.63e+03 | 7.80e+03 | 8.27e+03 | 5.49e+03 | 4.22e+03 | 4.45e+03 |
| TNF-a | 6 | 6 | 6 | 6 | 6 | 6 |
| IL-2 | 9 | 9 | 9 | 9 | 9 | 9 |
| IL-7 | 33 | 37 | 48 | 50 | 45 | 44 |
| IP-10 | 29 | 28 | 33 | 134 | 101 | 104 |
| IL-2R | 39 | 42 | 59 | 52 | 49 | 57 |
| MIG | 19 | 22 | 24 | 20 | 17 | 18 |
| IL-4 | 25 | 24 | 25 | 27 | 27 | 28 |
| IL-8 | 17.8e+03 | 17.8e+03 | 17.8e+03 | 17.8e+03 | 17.8e+03 | 17.8e+03 |

TABLE 10

Relative changes in WBC cytokine levels between mock and Dengue infections

| | MOI 0.1 | | | MOI 0.5 | | | MOI 2 | | |
|---|---|---|---|---|---|---|---|---|---|
| | 48 h | 72 h | 96 h | 48 h | 72 h | 96 h | 48 h | 72 h | 96 h |
| IL-1b | −33% | 0% | 0% | −33% | 0% | 6% | −22% | 11% | 11% |
| IL-10 | 0% | 0% | 8% | 8% | 17% | 42% | 8% | 17% | 25% |
| IL-13 | 0% | 0% | 0% | 0% | 0% | 0% | 0% | 0% | 0% |
| IL-6 | 9.20E+03% | 9.73E+03% | 8.56E+03% | 95.4E+03% | 10.1E+04% | 8.19E+03% | 12.02E+04% | 16.04E+04% | 12.46E+04% |
| IL-12 | 0% | 12% | 10% | 27% | 41% | 15% | 77% | 74% | 40% |
| Rantes | 41% | 0% | 0% | 347% | 27% | 0% | 1179% | 436% | 430% |
| CCL-11 | 0% | 0% | 0% | 0% | 0% | 0% | 0% | 0% | 0% |
| IL-17 | 0% | 0% | 0% | 0% | 0% | 0% | 0% | 0% | 0% |
| MIP-1a | 66% | 10% | −3% | 148% | 16% | −21% | 129% | 1% | −10% |
| GM-CSF | 0% | 0% | 0% | 20% | 0% | 0% | 320% | 153% | 173% |
| MIP-1b | 45% | 15% | −3% | 81% | 32% | −1% | 92% | 17% | −17% |
| MCP-1 | 543% | 325% | 262% | 1255% | 523% | 319% | 1774% | 523% | 319% |
| IL-15 | 0% | 0% | 0% | 0% | 0% | 0% | 93% | 39% | 45% |
| IL-5 | 0% | 0% | 0% | 117% | 79% | 96% | 158% | 133% | 138% |
| IFN-g | 20% | 20% | 11% | 60% | 53% | 11% | 93% | 47% | 11% |
| IFN-a | 163% | 85% | 72% | 260% | 133% | 116% | 415% | 166% | 135% |
| IL-1Ra | 39% | 7% | −6% | 49% | 7% | −26% | 16% | −31% | −56% |
| TNF-a | 33% | 0% | 0% | 122% | 0% | 0% | 239% | 0% | 0% |
| IL-2 | 0% | 0% | 0% | 0% | 0% | 0% | 0% | 0% | 0% |
| IL-7 | 140% | 188% | 121% | 320% | 408% | 392% | 363% | 496% | 479% |
| IP-10 | 367% | 308% | 325% | 933% | 883% | 650% | 4008% | 3367% | 2725% |
| IL-2R | 65% | 62% | 54% | 110% | 72% | 84% | 152% | 103% | 108% |
| MIG | −26% | −21% | −25% | −22% | −33% | −45% | −34% | −38% | −53% |
| IL-4 | 0% | 0% | 0% | 17% | 10% | 7% | 29% | 19% | 19% |
| IL-8 | 0% | 0% | 0% | 0% | 0% | 0% | 0% | 0% | 0% |

Example 8. Additional Virus Manufacturing Protocols

In addition to methods of Example 4, both Vero and FRhL cells are infected using dilutions of the supernatant from blind passage #2, DENV-2 #1710 and DNV-2 #1584, respectively. In order to increase the detection sensitivity, an immunofluorescence staining is developed to detect virus in the cells infected with supernatant from blind passage #2.

Ultracentrifugation is used to concentrate virus when necessary. Following confirmation of virus titer, final product is filtered to remove any cellular debris, assessed for absence of any adventitious organisms, and upon final lot released, bottled in 5 ml bottles, and stored at 4° C. until ready for shipment and administration.

Example 9. Collection of PBMC from Donors

Donors (either autologous or HLA-matched allogenic) have a leukapheresis procedure performed at a facility with trained personnel and proper equipment. After the apheresis is complete, the red cells, platelets, and plasma proteins are returned to the donor. The apheresis product is assessed at the site (Gram Stain test and Limulus Amoeba Lysis [LAL]) for presence of bacterial contamination. After passing, the collection container (with small testing sample container attached), is barcoded with donor-specific information and placed in an approved shipping container conforming to both FDA and DOT regulations for storage and shipping of non-infectious biological materials. The shipping container is packaged with a cooling element (e.g., solid $CO_2$, Liquid $N_2$), and temperature monitors. The shipping container is a hard plastic flask. A courier transports the container within 24 hours to the GMP manufacturing facility.

Example 10. Manufacture and Use of Dendritic Cells Pulsed with Tumor Antigens

Monocytes are separated from other collected white blood cells (e.g. T cells. B cells, NK cells, eosinophils and basophils). This is accomplished with immuno-magnetic selection or, alternatively, by adherence properties. Immunomagnetic selection involves pouring the white blood cells into a sterile plastic column with plastic beads coated with antibodies for immune cell CD surface proteins: (CD4/CD8/CD56, etc.).

An example of immunomagnetic selection is the EasySep Monocyte Enrichment kit available from Stem Cell Technologies (Vancouver, B.C, Canada, www.stemcell.com). To use the EasySep kit, the apheresis product is suspended in sterile PBS and poured into the EasySep plastic column containing Tetrameric antibody complexes with murine antibodies for: human CD2, CD3, CD16, CD19, CD20, CD56, CD66b, CD123, and Glycophorin A. After incubation for 10 minutes, EasySep magnetic particles are added. The cells adhering to the beads removed an electromagnet sorting. The magnet is inverted, and the desired cell fraction (monocytes), is poured into a sterile polystyrene flask for additional processing. Alternately, in a positive adherence selection assay, magnetic beads coated with CD1+/CD14+ antibodies is mixed with monocytes, a magnet is placed against the column, and non-binding cells are flushed out of the column with PBS solution. The monocytes are then washed off the beads. In positive adherence selection, the properties of monocytes to stick to certain surfaces are used to separate them by running the apheresis product down a slanted column.

Alternatively, bone marrow cells are depleted for lymphocytes and MHC Class positive cells by Fluorescent Activated Cell Sorting (FACS) with monoclonal antibodies for CD3, CD4, and CD8. Remaining cells are cultured overnight at 37° C. in a 5% $CO_2$ atmosphere in a basal cell culture medium supplemented with human AB serum. Human AB serum is chosen because it grows cells at a faster rate than other serum types, and serum free media produces DCs with much lower T-cell stimulation capability. After 24 hours, the cells are replated and cultured in the presence of Granulocyte-Macrophage Colony Stimulation Factor (GM-CSF), and recombinant IL-4 at 900 U/ml. After 3 to 4 days, media to be exchanged for fresh cytokine media.

Alternatively, dermal dendritic cells (DDCs) are prepared using the following methods: Keratomes from healthy human volunteers are incubated in a solution of the bacterial proteases Dispase type 2 at a final concentration of 1.2 U/ml in RPMI 1640 for 1 hour at 37° C. After the incubation period, epidermis and dermis are easily separated. Epidermal and dermal sheets are then cut into small (1-10 mm) pieces after several washing with PBS, and placed in RPMI 1640 supplemented with 10% Fetal Bovine Serum (FBS), and placed in 10-cm tissue culture plates. After 2-3 days, pieces of tissue are removed, and the medium collected. Cells migrating out of the tissue sections into the medium are spun down, resuspended in 1-2 ml fresh medium and stained with trypan blue. Further enrichment is achieved by separation on a metrizamide gradient. Cells are layered onto 3-ml columns of hypertonic 14.5% metrizamide and sedimented at 650 g for 10 minutes at room temperature. Low density interphase cells are collected and washed in two successively less hypertonic washes (RPMI 1640 with 10% FBS and 40 mM NaCl) to return cells to isotonicity.

When the monocytes are collected, they may number only a few thousand. The recombinant human growth factors rhuInterleukin-4 (IL-4), and rhuGranulocyte-Macrophage-Colony-Stimulation Factor (GM-CSF), are used in a multi-step protocol to accomplish the expansion of DC numbers to the range of 50 million. After the addition of IL-4 and GM-CSF, cells are assessed for and expansion in number and the development of mature-DC markers: ($CD11^+$, $CD80^+$, $CD83^+$), as well as increased expression of both Class I (for presentation of short peptides to $CD8^+$, and Class II MHC complexes (for presentation of longer peptides to $CD4^+$ Helper-Inducer T lymphocytes). After approximately 3-4 days, the number of mature DCs will be measured. For example, the monocyte-enriched fraction is placed in Nuclon-coated Cell Factory (Thermoscientific), with serum-free DC media (CellGro, Inc.), supplemented with GMP-2% human AB serum, 500 IU/ml (about 50 ng/ml) rhuIL-4 (CellGenix), with 500 IU/ml (about 50 ng/ml) rhuGM-CSF (CellGenix), added after the first 24 hours. Final product is approximately about 1 L of total media volume. After about 72 hours of culture, a population of immature DCs are assessed for the following markers: $CD1^+$ $CD11^+$ $CD14^+$.

Example 11. Pulsing the Dendritic Cells

A variety of tumor antigen sources are used for high-quality DCs: peptides, lysate from autologous tumors, whole tumor cells, and RNA coding for specific tumor antigens. An excisional biopsy or blood sample containing leukemic or lymphoma cells are obtained by surgery or blood draw followed by a magnetic selection to obtain leukemia/lymphoma cells. Once the tumor cells are obtained, they are barcoded and shipped in approved containers similar to those described for apheresis previously to the GMP facility. Samples may be frozen at −70° C. after passing bacterial contamination tests.

Whole autologous tumor cell lysate is prepared by several methods. To prepare the lysate, the tumor sample may be rewarmed to approximately 35° C. using a water bath or other procedure. The development of automated cell processors like the Miltenyi GentleMACS system allows the sample to be manually minced, suspended in PBS solution, then a pre-selected tissue-specific software-controlled rotor system separates the tumor cells. Cells are added to an enzyme mixture before being transferred to the Miltenyi GentleMACS dissociator. The single-cell suspension can be membrane-lysed with minimal damage to tumor peptides, using a hypochlorite solution, which will kill any residual tumor cells, neutralize $dT_H2$ cytokines, and increase immunogenicity for superior CTL affinity, avidity and activation. After adding hypochlorite, culture plates are incubated at 37 degrees Celsius, 5% $CO_2$, for 1 hour, with gentle manual agitation at 30 min to disperse hypochlorite. Cells are washed two time to neutralize the lysis reaction (e.g. with HBSS). Hypochlorite-treated cells may be subjected to subsequent freeze-thaw cycles. Alternatively, the sample does not separate the tumor cells. Instead the sample is left to contain tumor cells and supporting cells (e.g. cells from the tumor microenvironment). Cells are lysed with calcium hypochlorite to eliminate red blood cells and produce apoptotic and necrotic bodies without destroying peptides needed for CTL induction.

Lysate from the GentleMACS is added on the third day of immature DCs production. Immature DCs are co-cultured with tumor lysate for about 16 hours. The final step is maturation with an inflammatory signal. Clinical-Grade LPS (60 EU/ml) (R & D Invivogen), and Interferon-gamma (2000 IU/ml, about 100 ng/ml) (R&D Systems) are added to the flask and incubated for about 12 hours to mature the pulsed DC. After exposure to LPS, the DCs are assessed for up-regulation of CD80/CD83+ activation markers, and increase production of IL-12p70. In process testing at this stage includes sterility (as previously described), viability (% viable cells by Trypan Blue dye exclusion), and specificity (% DC measured by CD11c flow cytometry).

After final sterility, specificity, and viability assessment, the DCs are transferred to hard plastic containers suitable for freezing at −70'C in liquid $N_2$, storage up to 1 year, and shipping to the clinic for use. The containers are shipped cool overnight, then re-warmed to 37° C. in a warm-water bath before intravenous administration with a 0.9% NaCL solution concurrent over 30 minutes. The DCs are administered intravenously.

Example 12. Combination Delivery for Treatment of Cancer

Administration of the Dengue Virus is similar to that of other viral vaccine injections. A subject has an area of skin in the shoulder (deltoid) region cleaned with alcohol, then 0.5 ml of the virus is injected under the skin to mimic a mosquito bite. Once the subject has a fever the reaches 38.5° C., after 2-3 days from DV injection, the subject is infused by intralymphatic microcatheter with pulsed (primed) dendritic cells. Injections are repeated until the subject is negative for disease. DC fusions will use cells as manufactured in Example 6.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating or reducing melanoma, comprising:
   obtaining primed dendritic cells by a process comprising the steps of: contacting dendritic cells with a tumor antigen, lipopolysaccharide, R848, and interferon-gamma;
   administering the primed dendritic cells to a subject in need thereof; and
   administering a Dengue Virus to the subject, wherein the Dengue Virus is serotype 2 strain #1710, and wherein the subject has melanoma.

2. The method of claim 1, wherein the primed dendritic cells are administered intravenously.

3. The method of claim 1, wherein the tumor antigen is obtained from a cancer cell of the subject.

4. The method of claim 3, wherein the primed dendritic cells are autologous or allogenic to the subject.

5. The method of claim 1, wherein the primed dendritic cells produce 15 to 19 ng/mL of IL-12p70.

6. The method of claim 1, wherein the primed dendritic cells produce 15 to 23 ng/mL of IL-12p70.

7. The method of claim 1, wherein the subject is a human.

8. The method of claim 1, wherein the subject is a mouse.

9. The method of claim 1, wherein the primed dendritic cells are prepared by culturing on a hard surface.

10. The method of claim 9, wherein the hard surface is substantially free from a fluorinated polyethylene, a fluorinated polypropylene, or a phthalate.

11. The method of claim 1, wherein the Dengue Virus is isolated from a Vero cell line.

* * * * *